(12) United States Patent
Pollak et al.

(10) Patent No.: US 11,808,758 B2
(45) Date of Patent: *Nov. 7, 2023

(54) SAMPLE CARRIER FOR OPTICAL MEASUREMENTS

(71) Applicant: S.D. SIGHT DIAGNOSTICS LTD., Tel Aviv (IL)

(72) Inventors: Joseph Joel Pollak, Neve Daniel (IL); Sarah Levy Schreier, Jaffa (IL); Yochay Shlomo Eshel, Sde Warburg (IL); Amir Zait, Binyamina (IL); Sharon Pecker, Rehovot (IL); Trevor Ruggiero, Somerville, MA (US)

(73) Assignee: S.D. Sight Diagnostics Ltd., Tel Aviv (IL)

( * ) Notice: Subject to any disclaimer, the term of this patent is extended or adjusted under 35 U.S.C. 154(b) by 266 days.

This patent is subject to a terminal disclaimer.

(21) Appl. No.: 17/082,483

(22) Filed: Oct. 28, 2020

(65) Prior Publication Data
US 2021/0072226 A1 Mar. 11, 2021

Related U.S. Application Data

(63) Continuation of application No. 16/098,893, filed as application No. PCT/IL2017/050523 on May 11, 2017, now Pat. No. 11,307,196.
(Continued)

(51) Int. Cl.
*G01N 33/50* (2006.01)
*G01N 21/31* (2006.01)
(Continued)

(52) U.S. Cl.
CPC ......... *G01N 33/50* (2013.01); *G01N 21/0303* (2013.01); *G01N 21/31* (2013.01);
(Continued)

(58) Field of Classification Search
None
See application file for complete search history.

(56) References Cited

U.S. PATENT DOCUMENTS

| 3,203,768 A | 8/1965 | Tiller et al. |
| 3,603,156 A | 9/1971 | Konkol |

(Continued)

FOREIGN PATENT DOCUMENTS

| CA | 2655024 | 1/2008 |
| CN | 1918501 A | 2/2007 |

(Continued)

OTHER PUBLICATIONS

Saraswat, et al. "Automated microscopic image analysis for leukocytes identification: A survey", ABV—Indian Institute of Information Technology and Management, Gwalior, India, Micron, 2014, vol. 65, pp. 20-33.

(Continued)

*Primary Examiner* — Xiaoyun R Xu
(74) *Attorney, Agent, or Firm* — Sughrue Mion, PLLC

(57) ABSTRACT

Apparatus and methods are described including placing a sample into a sample carrier that comprises a plurality of regions having upper and lower surfaces, having respective heights that are different from each other, and being configured such that cells form a monolayer, the monolayer within respective regions of the sample carrier having respective, different densities from each other, due to the respective regions of the sample carrier having respective heights that are different from each other. Microscopic images are acquired of each of the plurality of regions. Measurements are performed upon cell types that have a relatively high density upon microscopic images of a region of the sample chamber having a relatively low height, and measurements are performed upon cell types that have a relatively low density upon microscopic images of a region (Continued)

of the sample chamber having a relatively great height. Other applications are also described.

9 Claims, 4 Drawing Sheets

Related U.S. Application Data

(60) Provisional application No. 62/334,521, filed on May 11, 2016.

(51) Int. Cl.
  *G01N 21/59* (2006.01)
  *G01N 21/64* (2006.01)
  *G01N 21/03* (2006.01)

(52) U.S. Cl.
  CPC .............. *G01N 21/59* (2013.01); *G01N 21/64* (2013.01); *G01N 2201/0662* (2013.01)

(56) References Cited

U.S. PATENT DOCUMENTS

| | | |
|---|---|---|
| 3,676,076 A | 7/1972 | Grady |
| 3,786,184 A | 1/1974 | Pieters |
| 3,916,205 A | 10/1975 | Kleinerman |
| 3,967,056 A | 6/1976 | Yata et al. |
| 4,030,888 A | 6/1977 | Yamamoto |
| 4,076,419 A | 2/1978 | Kleker |
| 4,097,845 A | 6/1978 | Bacus |
| 4,199,748 A | 4/1980 | Bacus |
| 4,209,548 A | 6/1980 | Bacus |
| 4,350,884 A | 9/1982 | Dieter |
| 4,453,266 A | 6/1984 | Bacus |
| 4,454,235 A | 6/1984 | Johnson |
| 4,494,479 A | 1/1985 | Drury et al. |
| 4,580,895 A | 4/1986 | Patel |
| 4,700,298 A | 10/1987 | Palcic et al. |
| 4,761,381 A | 8/1988 | Blatt et al. |
| 4,774,192 A | 9/1988 | Terminiello et al. |
| 4,803,352 A | 2/1989 | Bierleutgeb |
| 4,849,340 A | 7/1989 | Oberhardt |
| 4,851,330 A | 7/1989 | Kohne |
| 4,902,101 A | 2/1990 | Fujihara et al. |
| 5,001,067 A | 3/1991 | Coleman et al. |
| 5,064,282 A | 11/1991 | Curtis |
| 5,229,265 A | 7/1993 | Tometsko |
| 5,300,779 A | 4/1994 | Hillman et al. |
| 5,331,958 A | 7/1994 | Oppenheimer |
| 5,430,542 A | 7/1995 | Shepherd et al. |
| 5,470,751 A | 11/1995 | Sakata et al. |
| 5,566,249 A | 10/1996 | Rosenlof et al. |
| 5,625,706 A | 4/1997 | Lee et al. |
| 5,663,057 A | 9/1997 | Drocourt et al. |
| 5,671,288 A | 9/1997 | Wilhelm et al. |
| 5,672,861 A | 9/1997 | Fairley et al. |
| 5,674,457 A | 10/1997 | Williamsson et al. |
| 5,745,804 A | 4/1998 | Iwane |
| 5,782,770 A | 7/1998 | Mooradian et al. |
| 5,827,190 A | 10/1998 | Palcic et al. |
| 5,834,217 A | 11/1998 | Levine et al. |
| 5,932,872 A | 8/1999 | Price |
| 5,948,686 A | 9/1999 | Wardlaw |
| 5,978,497 A | 11/1999 | Lee et al. |
| 5,985,595 A | 11/1999 | Krider et al. |
| 6,005,964 A | 12/1999 | Reid et al. |
| 6,027,695 A | 2/2000 | Oldenburg et al. |
| 6,064,474 A | 5/2000 | Lee et al. |
| 6,074,879 A | 6/2000 | Zelmanovic et al. |
| 6,101,404 A | 8/2000 | Yoon et al. |
| 6,235,536 B1 | 5/2001 | Wardlaw |
| 6,262,798 B1 | 7/2001 | Shepherd et al. |
| 6,320,979 B1 | 11/2001 | Melen |
| 6,330,348 B1 | 12/2001 | Kerschmann et al. |
| 6,339,472 B1 | 1/2002 | Hafeman |
| 6,350,613 B1 | 2/2002 | Wardlaw et al. |
| 6,448,024 B1 | 9/2002 | Bruegger |
| 6,519,355 B2 | 2/2003 | Nelson |
| 6,554,788 B1 | 4/2003 | Hunley et al. |
| 6,582,964 B1 | 6/2003 | Samsoondar et al. |
| 6,611,777 B2 | 8/2003 | Samsoondar |
| 6,632,681 B1 | 10/2003 | Chu |
| 6,658,143 B2 | 12/2003 | Hansen et al. |
| 6,664,528 B1 | 12/2003 | Cartlidge et al. |
| 6,711,516 B2 | 3/2004 | Samsoondar |
| 6,799,119 B1 | 9/2004 | Voorhees et al. |
| 6,819,408 B1 | 11/2004 | Scrivens et al. |
| 6,831,733 B2 | 12/2004 | Pettersson et al. |
| 6,834,237 B2 | 12/2004 | Noergaard et al. |
| 6,836,559 B2 | 12/2004 | Abdel-Fattah et al. |
| 6,842,233 B2 | 1/2005 | Narisada et al. |
| 6,866,823 B2 | 3/2005 | Wardlaw |
| 6,872,930 B2 | 3/2005 | Cartlidge et al. |
| 6,898,451 B2 | 5/2005 | Wuori |
| 6,903,323 B2 | 6/2005 | Cartlidge et al. |
| 6,929,953 B1 | 8/2005 | Wardlaw |
| 6,949,384 B2 | 9/2005 | Samsoondar |
| 6,955,872 B2 | 10/2005 | Maples et al. |
| 6,956,650 B2 | 10/2005 | Boas et al. |
| 6,989,891 B2 | 1/2006 | Braig et al. |
| 7,027,628 B1 | 4/2006 | Gagnon et al. |
| 7,030,351 B2 | 4/2006 | Wasserman et al. |
| 7,034,883 B1 | 4/2006 | Rosenqvist |
| 7,105,795 B2 | 9/2006 | Cartlidge et al. |
| 7,132,636 B1 | 11/2006 | Cartlidge et al. |
| 7,133,547 B2 | 11/2006 | Marcelpoil et al. |
| 7,151,246 B2 | 12/2006 | Fein et al. |
| 7,155,049 B2 | 12/2006 | Wetzel et al. |
| 7,248,716 B2 | 7/2007 | Fein et al. |
| 7,274,810 B2 | 9/2007 | Reeves et al. |
| 7,283,217 B2 | 10/2007 | Ikeuchi et al. |
| 7,288,751 B2 | 10/2007 | Cartlidge et al. |
| 7,305,109 B1 | 12/2007 | Gagnon et al. |
| 7,324,694 B2 | 1/2008 | Chapoulaud et al. |
| 7,329,537 B2 | 2/2008 | Qiu |
| 7,338,168 B2 | 3/2008 | Cartlidge et al. |
| 7,344,890 B2 | 3/2008 | Perez et al. |
| 7,346,205 B2 | 3/2008 | Walker, Jr. |
| 7,369,696 B2 | 5/2008 | Arini et al. |
| 7,385,168 B2 | 6/2008 | Cartlidge et al. |
| 7,387,898 B1 | 6/2008 | Gordon |
| 7,411,680 B2 | 8/2008 | Chang et al. |
| 7,417,213 B2 | 8/2008 | Krief et al. |
| 7,425,421 B2 | 9/2008 | Dertinger |
| 7,439,478 B2 | 10/2008 | Cartlidge et al. |
| 7,450,223 B2 | 11/2008 | Ikeuchi et al. |
| 7,450,762 B2 | 11/2008 | Morell |
| 7,460,222 B2 | 12/2008 | Kalveram et al. |
| 7,490,085 B2 | 2/2009 | Walker et al. |
| 7,493,219 B1 | 2/2009 | Qi et al. |
| 7,580,120 B2 | 8/2009 | Hamada et al. |
| 7,599,893 B2 | 10/2009 | Sapir et al. |
| 7,601,938 B2 | 10/2009 | Cartlidge et al. |
| 7,602,954 B2 | 10/2009 | Marcelpoil et al. |
| 7,605,356 B2 | 10/2009 | Krief et al. |
| 7,609,369 B2 | 10/2009 | Simon-Lopez |
| 7,630,063 B2 | 12/2009 | Padmanabhan et al. |
| 7,633,604 B2 | 12/2009 | Ikeuchi et al. |
| 7,638,748 B2 | 12/2009 | Krief et al. |
| 7,663,738 B2 | 2/2010 | Johansson |
| 7,668,362 B2 | 2/2010 | Olson et al. |
| 7,692,131 B2 | 4/2010 | Fein et al. |
| 7,697,764 B2 | 4/2010 | Kataoka |
| 7,702,181 B2 | 4/2010 | Gouch |
| 7,706,862 B2 | 4/2010 | Alfano et al. |
| 7,713,474 B2 | 5/2010 | Schulman et al. |
| 7,747,153 B2 | 6/2010 | Ibaraki |
| 7,765,069 B2 | 6/2010 | Ostoich et al. |
| 7,777,869 B2 | 8/2010 | Nerin et al. |
| 7,787,109 B2 | 8/2010 | Dosmann et al. |
| 7,796,797 B2 | 9/2010 | Nakaya et al. |
| 7,863,552 B2 | 1/2011 | Cartlidge et al. |
| 7,869,009 B2 | 1/2011 | Dosmann et al. |

(56) References Cited

U.S. PATENT DOCUMENTS

| | | |
|---|---|---|
| 7,894,047 B2 | 2/2011 | Hamada et al. |
| 7,911,617 B2 | 3/2011 | Padmanabhan et al. |
| 7,925,070 B2 | 4/2011 | Sumida et al. |
| 7,929,121 B2 | 4/2011 | Wardlaw et al. |
| 7,933,435 B2 | 4/2011 | Hunter et al. |
| 7,936,913 B2 | 5/2011 | Nordell et al. |
| 7,951,599 B2 | 5/2011 | Levine et al. |
| 7,995,200 B2 | 8/2011 | Matsumoto |
| 7,998,435 B2 | 8/2011 | Reed |
| 8,000,511 B2 | 8/2011 | Perz |
| 8,044,974 B2 | 10/2011 | Sumida et al. |
| 8,045,782 B2 | 10/2011 | Li et al. |
| 8,055,471 B2 | 11/2011 | Qi et al. |
| 8,064,680 B2 | 11/2011 | Ramoser et al. |
| 8,077,296 B2 | 12/2011 | Wardlaw et al. |
| 8,081,303 B2 | 12/2011 | Levine et al. |
| 8,105,554 B2 | 1/2012 | Kanigan et al. |
| 8,125,643 B2 | 2/2012 | Hansen et al. |
| D655,421 S | 3/2012 | Lee et al. |
| 8,131,035 B2 | 3/2012 | Grady et al. |
| 8,131,052 B2 | 3/2012 | Alexandrov |
| 8,150,114 B2 | 4/2012 | Svanberg et al. |
| 8,154,713 B2 | 4/2012 | Simon-Lopez |
| 8,165,385 B2 | 4/2012 | Reeves et al. |
| 8,175,353 B2 | 5/2012 | Westphal et al. |
| 8,179,597 B2 | 5/2012 | Namba et al. |
| 8,184,273 B2 | 5/2012 | Dosmann et al. |
| 8,192,995 B2 | 6/2012 | Zhang et al. |
| 8,216,832 B2 | 7/2012 | Battrell et al. |
| 8,224,058 B2 | 7/2012 | Lindberg et al. |
| 8,269,954 B2 | 9/2012 | Levine et al. |
| 8,280,134 B2 | 10/2012 | Hoyt |
| 8,310,659 B2 | 11/2012 | Wardlaw et al. |
| 8,320,655 B2 | 11/2012 | Sarachan et al. |
| 8,327,724 B2 | 12/2012 | Fairs et al. |
| 8,331,642 B2 | 12/2012 | Zerfass et al. |
| 8,339,586 B2 | 12/2012 | Zahniser et al. |
| 8,345,227 B2 | 1/2013 | Zahniser et al. |
| 8,351,676 B2 | 1/2013 | Dai et al. |
| 8,363,221 B2 | 1/2013 | Hansen et al. |
| 8,379,944 B2 | 2/2013 | Grady et al. |
| 8,406,498 B2 | 3/2013 | Ortyn et al. |
| 8,428,331 B2 | 4/2013 | DiMarzio et al. |
| 8,432,392 B2 | 4/2013 | Kim et al. |
| 8,477,294 B2 | 7/2013 | Zahniser et al. |
| 8,481,303 B2 | 7/2013 | Faris et al. |
| 8,488,111 B2 | 7/2013 | Zahniser et al. |
| 8,491,499 B2 | 7/2013 | Choi et al. |
| 8,526,704 B2 | 9/2013 | Dobbe |
| 8,570,496 B2 | 10/2013 | Chen |
| 8,582,924 B2 | 11/2013 | De La Torre-Bueno et al. |
| 8,638,427 B2 | 1/2014 | Wardlaw et al. |
| 8,712,142 B2 | 4/2014 | Rajpoot et al. |
| 8,736,824 B2 | 5/2014 | Matsui et al. |
| 8,744,165 B2 | 6/2014 | Liu et al. |
| 8,778,687 B2 | 7/2014 | Levine et al. |
| 8,787,650 B2 | 7/2014 | Muragame |
| 8,792,693 B2 | 7/2014 | Satish et al. |
| 8,837,803 B2 | 9/2014 | Wang et al. |
| 8,849,024 B2 | 9/2014 | Shinoda et al. |
| 8,873,827 B2 | 10/2014 | McCulloch et al. |
| 8,877,458 B2 | 11/2014 | Maurer |
| 8,878,923 B2 | 11/2014 | Henderson et al. |
| 8,885,154 B2 | 11/2014 | Wardlaw et al. |
| 8,885,912 B2 | 11/2014 | Sui |
| 8,891,851 B2 | 11/2014 | Spaulding |
| 8,922,761 B2 | 12/2014 | Zahniser et al. |
| 8,942,458 B2 | 1/2015 | Takahashi et al. |
| 8,964,171 B2 | 2/2015 | Zahniser et al. |
| 8,992,750 B1 | 3/2015 | Beaty |
| 8,994,930 B2 | 3/2015 | Levine et al. |
| 9,012,868 B2 | 4/2015 | Courtney et al. |
| 9,041,792 B2 | 5/2015 | Van Leeuwen et al. |
| 9,046,473 B2 | 6/2015 | Levine et al. |
| 9,050,595 B2 | 6/2015 | Miller et al. |
| 9,064,301 B2 | 6/2015 | Zie et al. |
| 9,176,121 B2 | 11/2015 | Winkelman et al. |
| 9,186,843 B2 | 11/2015 | Chan et al. |
| 9,240,043 B2 | 1/2016 | Christiansen et al. |
| 9,322,767 B2 | 4/2016 | Ehrenkranz |
| 9,329,129 B2 | 5/2016 | Pollak et al. |
| 9,342,734 B2 | 5/2016 | Lin et al. |
| 9,404,852 B2 | 8/2016 | Braig et al. |
| 9,470,609 B2 | 10/2016 | Wimberger-Friedl et al. |
| 9,477,875 B2 | 10/2016 | Ohya et al. |
| 9,522,396 B2 | 12/2016 | Bachelet et al. |
| 9,528,978 B2 | 12/2016 | Yamada |
| 9,588,033 B2 | 3/2017 | Zahniser et al. |
| 9,767,343 B1 | 9/2017 | Jones et al. |
| 9,820,990 B2 | 11/2017 | Pak et al. |
| 9,933,363 B2 | 4/2018 | Danuser et al. |
| 9,934,571 B2 | 4/2018 | Ozaki et al. |
| 9,976,945 B2 | 5/2018 | Kendall et al. |
| 10,024,858 B2 | 7/2018 | Smith et al. |
| 10,061,972 B2 | 8/2018 | Champlin et al. |
| 10,093,957 B2 | 10/2018 | Pollak et al. |
| 10,169,861 B2 | 1/2019 | Ozaki et al. |
| 10,176,565 B2 | 1/2019 | Greenfield et al. |
| 10,281,386 B2 | 5/2019 | Hsu et al. |
| 10,482,595 B2 | 11/2019 | Yorav-Raphael |
| 10,488,644 B2 | 11/2019 | Eshel et al. |
| 10,508,983 B2 | 12/2019 | Kendall et al. |
| 10,640,807 B2 | 5/2020 | Pollak et al. |
| 10,663,712 B2 | 5/2020 | Eshel et al. |
| 10,843,190 B2 | 11/2020 | Bachelet et al. |
| 11,199,690 B2 | 12/2021 | Eshel et al. |
| 2002/0009711 A1 | 1/2002 | Wada et al. |
| 2002/0028158 A1 | 3/2002 | Wardlaw |
| 2002/0028471 A1 | 3/2002 | Oberhardt |
| 2003/0017085 A1 | 1/2003 | Kercso et al. |
| 2003/0161514 A1 | 8/2003 | Curry |
| 2003/0170613 A1 | 9/2003 | Straus |
| 2003/0197925 A1 | 10/2003 | Hamborg |
| 2003/0224522 A1 | 12/2003 | de Jong et al. |
| 2003/0227612 A1 | 12/2003 | Fein et al. |
| 2003/0227673 A1 | 12/2003 | Nakagawa |
| 2003/0231791 A1 | 12/2003 | Torre-Bueno et al. |
| 2004/0004614 A1 | 1/2004 | Bacus et al. |
| 2004/0122216 A1 | 6/2004 | Nielsen et al. |
| 2004/0132171 A1 | 7/2004 | Rule et al. |
| 2004/0170312 A1 | 9/2004 | Soenksen |
| 2004/0185447 A1 | 9/2004 | Maples et al. |
| 2004/0218804 A1 | 11/2004 | Affleck et al. |
| 2004/0240050 A1 | 12/2004 | Ogihara |
| 2004/0241677 A1 | 12/2004 | Lin et al. |
| 2005/0089208 A1 | 4/2005 | Dong et al. |
| 2005/0109959 A1 | 5/2005 | Wasserman et al. |
| 2005/0175992 A1 | 8/2005 | Aberl et al. |
| 2005/0286800 A1 | 12/2005 | Gouch |
| 2006/0002817 A1 | 1/2006 | Bohm et al. |
| 2006/0003458 A1 | 1/2006 | Golovchenko et al. |
| 2006/0045505 A1 | 3/2006 | Zeineh et al. |
| 2006/0051778 A1 | 3/2006 | Kallick |
| 2006/0063185 A1 | 3/2006 | Vannier |
| 2006/0079144 A1 | 4/2006 | Klisch et al. |
| 2006/0187442 A1 | 8/2006 | Chang et al. |
| 2006/0190226 A1 | 8/2006 | Jojic et al. |
| 2006/0222567 A1 | 10/2006 | Kloepfer et al. |
| 2006/0223052 A1 | 10/2006 | MacDonald et al. |
| 2006/0223165 A1 | 10/2006 | Chang et al. |
| 2007/0054350 A1 | 3/2007 | Walker |
| 2007/0076190 A1 | 4/2007 | Nakaya et al. |
| 2007/0161075 A1 | 7/2007 | Gleich |
| 2007/0172956 A1 | 7/2007 | Magari et al. |
| 2007/0243117 A1 | 10/2007 | Wardlaw |
| 2007/0250301 A1 | 10/2007 | Vaisberg et al. |
| 2007/0252984 A1 | 11/2007 | Van Beek et al. |
| 2008/0019584 A1 | 1/2008 | Lindberg et al. |
| 2008/0020128 A1 | 1/2008 | van Ryper et al. |
| 2008/0059135 A1 | 3/2008 | Murugkar et al. |
| 2008/0118399 A1 | 5/2008 | Fleming |
| 2008/0187466 A1* | 8/2008 | Wardlaw .................. B01L 3/50 422/400 |
| 2008/0212069 A1 | 9/2008 | Goldberg et al. |

(56) References Cited

U.S. PATENT DOCUMENTS

| | | |
|---|---|---|
| 2008/0260369 A1 | 10/2008 | Ibaraki |
| 2008/0273776 A1 | 11/2008 | Krief et al. |
| 2008/0305514 A1 | 12/2008 | Alford et al. |
| 2009/0066934 A1 | 3/2009 | Gao et al. |
| 2009/0074282 A1 | 3/2009 | Pinard et al. |
| 2009/0075324 A1 | 3/2009 | Pettersson |
| 2009/0086314 A1 | 4/2009 | Namba et al. |
| 2009/0088336 A1 | 4/2009 | Burd et al. |
| 2009/0128618 A1 | 5/2009 | Fahn et al. |
| 2009/0185734 A1 | 7/2009 | Lindberg et al. |
| 2009/0191098 A1 | 7/2009 | Beard et al. |
| 2009/0195688 A1 | 8/2009 | Henderson et al. |
| 2009/0213214 A1 | 8/2009 | Yamada |
| 2009/0258347 A1 | 10/2009 | Scott |
| 2009/0269799 A1 | 10/2009 | Winkelman et al. |
| 2009/0291854 A1 | 11/2009 | Wiesinger-Mayr et al. |
| 2010/0003265 A1 | 1/2010 | Scheffler et al. |
| 2010/0068747 A1 | 3/2010 | Herrenknecht |
| 2010/0104169 A1 | 4/2010 | Yamada |
| 2010/0112631 A1 | 5/2010 | Hur et al. |
| 2010/0120129 A1 | 5/2010 | Amshey et al. |
| 2010/0136556 A1 | 6/2010 | Friedberger et al. |
| 2010/0136570 A1 | 6/2010 | Goldberg et al. |
| 2010/0152054 A1 | 6/2010 | Love et al. |
| 2010/0157086 A1 | 6/2010 | Segale et al. |
| 2010/0172020 A1 | 7/2010 | Price et al. |
| 2010/0192706 A1 | 8/2010 | Fairs et al. |
| 2010/0232675 A1 | 9/2010 | Ortyn et al. |
| 2010/0234703 A1 | 9/2010 | Sterling et al. |
| 2010/0253907 A1 | 10/2010 | Korb et al. |
| 2010/0254596 A1 | 10/2010 | Xiong et al. |
| 2010/0256918 A1 | 10/2010 | Chen et al. |
| 2010/0265323 A1 | 10/2010 | Perz |
| 2010/0272334 A1 | 10/2010 | Yamada et al. |
| 2010/0295998 A1 | 11/2010 | Sakai et al. |
| 2010/0300563 A1 | 12/2010 | Ramunas et al. |
| 2011/0007178 A1 | 1/2011 | Kahlman |
| 2011/0009163 A1 | 1/2011 | Fletcher et al. |
| 2011/0030458 A1 | 2/2011 | Park et al. |
| 2011/0059481 A1 | 3/2011 | Wardlaw et al. |
| 2011/0102571 A1 | 5/2011 | Yoneyama |
| 2011/0123398 A1 | 5/2011 | Carrilho et al. |
| 2011/0144480 A1 | 6/2011 | Lu et al. |
| 2011/0149097 A1 | 6/2011 | Danuser et al. |
| 2011/0151502 A1 | 6/2011 | Kendall et al. |
| 2011/0178716 A1 | 7/2011 | Krockenberger et al. |
| 2011/0212486 A1 | 9/2011 | Yamada et al. |
| 2011/0243794 A1 | 10/2011 | Wardlaw |
| 2011/0249910 A1 | 10/2011 | Henderson et al. |
| 2011/0275111 A1 | 11/2011 | Pettigrew et al. |
| 2011/0301012 A1 | 12/2011 | Dolecek et al. |
| 2012/0002195 A1 | 1/2012 | Wu et al. |
| 2012/0021951 A1 | 1/2012 | Hess et al. |
| 2012/0030618 A1 | 2/2012 | Leong et al. |
| 2012/0044342 A1 | 2/2012 | Hing et al. |
| 2012/0058504 A1 | 3/2012 | Li et al. |
| 2012/0092477 A1 | 4/2012 | Kawano et al. |
| 2012/0120221 A1 | 5/2012 | Dong et al. |
| 2012/0169863 A1 | 7/2012 | Bachelet et al. |
| 2012/0225446 A1 | 9/2012 | Wimberger-Friedl et al. |
| 2012/0237107 A1 | 9/2012 | Tawfik et al. |
| 2012/0275671 A1 | 11/2012 | Eichhorn et al. |
| 2012/0312957 A1 | 12/2012 | Loney et al. |
| 2012/0320045 A1 | 12/2012 | Yao et al. |
| 2013/0023007 A1 | 1/2013 | Zahniser et al. |
| 2013/0078668 A1 | 3/2013 | Levine et al. |
| 2013/0130262 A1 | 5/2013 | Battrell et al. |
| 2013/0169948 A1 | 7/2013 | Xie et al. |
| 2013/0170730 A1 | 7/2013 | Yu et al. |
| 2013/0176551 A1 | 7/2013 | Wardlaw et al. |
| 2013/0177974 A1 | 7/2013 | Mamaghani et al. |
| 2013/0203082 A1 | 8/2013 | Gonda et al. |
| 2013/0273968 A1 | 10/2013 | Rhoads et al. |
| 2013/0284924 A1 | 10/2013 | Mizuochi et al. |
| 2013/0290225 A1 | 10/2013 | Kamath et al. |
| 2013/0323757 A1 | 12/2013 | Poher et al. |
| 2014/0139625 A1 | 5/2014 | Mathuis et al. |
| 2014/0139630 A1 | 5/2014 | Kowalevicz |
| 2014/0185906 A1 | 7/2014 | Ding et al. |
| 2014/0186859 A1 | 7/2014 | Calderwood et al. |
| 2014/0205176 A1 | 7/2014 | Obrien et al. |
| 2014/0270425 A1 | 9/2014 | Kenny et al. |
| 2014/0347459 A1 | 11/2014 | Greenfield et al. |
| 2014/0347463 A1 | 11/2014 | Lin et al. |
| 2014/0353524 A1 | 12/2014 | Danuser et al. |
| 2015/0037806 A1 | 2/2015 | Pollak et al. |
| 2015/0124082 A1 | 5/2015 | Kato et al. |
| 2015/0183153 A1 | 7/2015 | Chan et al. |
| 2015/0190063 A1 | 7/2015 | Zakharov et al. |
| 2015/0246170 A1 | 9/2015 | Miao et al. |
| 2015/0278575 A1 | 10/2015 | Allano et al. |
| 2015/0302237 A1 | 10/2015 | Ohya et al. |
| 2015/0316477 A1 | 11/2015 | Pollak et al. |
| 2016/0042507 A1 | 2/2016 | Turner |
| 2016/0187235 A1 | 6/2016 | Fine |
| 2016/0208306 A1 | 7/2016 | Pollak et al. |
| 2016/0246046 A1 | 8/2016 | Yorav Raphael et al. |
| 2016/0250312 A1 | 9/2016 | Longley et al. |
| 2016/0279633 A1 | 9/2016 | Bachelet et al. |
| 2017/0052110 A1 | 2/2017 | Malissek et al. |
| 2017/0115271 A1 | 4/2017 | Xie et al. |
| 2017/0160185 A1 | 6/2017 | Minemura et al. |
| 2017/0191945 A1 | 7/2017 | Zhang et al. |
| 2017/0218425 A1 | 8/2017 | Chen et al. |
| 2017/0292905 A1 | 10/2017 | Obrien et al. |
| 2017/0307496 A1 | 10/2017 | Zahniser et al. |
| 2017/0326549 A1 | 11/2017 | Jones et al. |
| 2017/0328924 A1 | 11/2017 | Jones et al. |
| 2018/0246313 A1 | 8/2018 | Eshel et al. |
| 2018/0296102 A1 | 10/2018 | Satish et al. |
| 2018/0297024 A1 | 10/2018 | Tran |
| 2019/0002950 A1 | 1/2019 | Pollak et al. |
| 2019/0087953 A1 | 3/2019 | Yorav-Raphael et al. |
| 2019/0130567 A1 | 5/2019 | Greenfield et al. |
| 2019/0145963 A1 | 5/2019 | Zait et al. |
| 2019/0302099 A1 | 10/2019 | Pollak et al. |
| 2019/0347467 A1 | 11/2019 | Ohsaka et al. |
| 2020/0034967 A1 | 1/2020 | Yorav-Raphael et al. |
| 2020/0049970 A1 | 2/2020 | Eshel et al. |
| 2020/0111209 A1 | 4/2020 | Greenfield et al. |
| 2020/0249458 A1 | 8/2020 | Eshel et al. |
| 2020/0300750 A1 | 9/2020 | Eshel et al. |
| 2022/0189016 A1 | 6/2022 | Barnes et al. |

FOREIGN PATENT DOCUMENTS

| | | |
|---|---|---|
| CN | 101501785 A | 8/2009 |
| CN | 101403650 | 4/2010 |
| CN | 102282467 A | 12/2011 |
| EP | 0073551 | 3/1983 |
| EP | 0479231 | 4/1992 |
| EP | 1 381 229 A1 | 1/2004 |
| EP | 1698883 | 9/2006 |
| EP | 2145684 | 1/2010 |
| EP | 3001174 | 3/2016 |
| EP | 3 123 927 A1 | 2/2017 |
| EP | 2211165 B1 | 7/2017 |
| EP | 3482189 A1 | 5/2019 |
| EP | 1 873 232 B1 | 2/2020 |
| GB | 2329014 A | 3/1999 |
| JP | 60-162955 A | 8/1985 |
| JP | 61-198204 | 9/1986 |
| JP | 7-504038 A | 4/1995 |
| JP | H08-313340 A | 11/1996 |
| JP | 9-54083 A | 2/1997 |
| JP | H11-73903 | 3/1999 |
| JP | 2000-199845 | 7/2000 |
| JP | 2002-516982 A | 6/2002 |
| JP | 2004-144526 A | 5/2004 |
| JP | 2004-257768 | 9/2004 |
| JP | 2006-506607 A | 2/2006 |
| JP | 2006-301270 | 11/2006 |
| JP | 2007040814 | 2/2007 |
| JP | 2009-180539 A | 8/2009 |

(56) References Cited

FOREIGN PATENT DOCUMENTS

| | | |
|---|---|---|
| JP | 2009-233927 A | 10/2009 |
| JP | 2009-268432 A | 11/2009 |
| JP | 2011-95225 A | 5/2011 |
| JP | 2013-515264 A | 5/2013 |
| JP | 2013-541767 A | 11/2013 |
| JP | 2014-41139 A | 3/2014 |
| JP | 2015-57600 A | 3/2015 |
| JP | 2016-70658 A | 5/2016 |
| JP | 2016-528506 A | 9/2016 |
| JP | 2017-209530 A | 11/2017 |
| JP | 2018-525611 A | 9/2018 |
| RU | 2402006 C1 | 10/2010 |
| WO | 8505446 A1 | 12/1985 |
| WO | 96/01438 | 1/1996 |
| WO | 1996/012981 | 5/1996 |
| WO | 9613615 A1 | 5/1996 |
| WO | 0006765 A1 | 2/2000 |
| WO | 2000/055572 | 9/2000 |
| WO | 0052195 A1 | 9/2000 |
| WO | 03/056327 | 7/2003 |
| WO | 2003/065358 A2 | 8/2003 |
| WO | 2003/073365 | 9/2003 |
| WO | 03/081525 A1 | 10/2003 |
| WO | 2004/020112 A1 | 3/2004 |
| WO | 2004/111610 | 12/2004 |
| WO | 2005/121863 | 12/2005 |
| WO | 2006/121266 | 11/2006 |
| WO | 2008/063135 | 5/2008 |
| WO | 2010/036827 A1 | 4/2010 |
| WO | 2010/056740 | 5/2010 |
| WO | 2010/116341 A1 | 10/2010 |
| WO | 2010/126903 | 11/2010 |
| WO | 2010/137543 A1 | 12/2010 |
| WO | 2011/056658 A1 | 5/2011 |
| WO | 2011/076413 A1 | 6/2011 |
| WO | 2011/123070 A1 | 10/2011 |
| WO | 2011/143075 | 11/2011 |
| WO | 2012/000102 | 1/2012 |
| WO | 2012/029269 A | 3/2012 |
| WO | 2012/030313 | 3/2012 |
| WO | 2012/090198 | 7/2012 |
| WO | 2012/154333 | 11/2012 |
| WO | 2013/041951 A1 | 3/2013 |
| WO | 2013/098821 | 7/2013 |
| WO | 2014/159620 | 10/2014 |
| WO | 2014/188405 | 11/2014 |
| WO | 2015/001553 | 1/2015 |
| WO | 2015/029032 | 3/2015 |
| WO | 2015/089632 A1 | 6/2015 |
| WO | 2016/030897 | 3/2016 |
| WO | 2016/203320 A2 | 12/2016 |
| WO | 2017/046799 | 3/2017 |
| WO | 2017/168411 A1 | 10/2017 |
| WO | 2017/195205 A1 | 11/2017 |
| WO | 2017/195208 A1 | 11/2017 |
| WO | 2018/009920 A1 | 1/2018 |
| WO | 2018/102748 A1 | 6/2018 |
| WO | 2019/035084 A1 | 2/2019 |
| WO | 2019/097387 A1 | 5/2019 |
| WO | 2019/102277 A1 | 5/2019 |
| WO | 2019/198094 A1 | 10/2019 |
| WO | 2021/079305 A1 | 4/2021 |
| WO | 2021/079306 A1 | 4/2021 |

OTHER PUBLICATIONS

Hiremath, P. S,. et al., "Automated Identification and Classification of White Blood Cells (Leukocytes) in Digital Microscopic Images", IJCA Special Issue on "Recent Trends in Image Processing and Pattern Recognition" RTIPPR, 2010, pp. 59-63.

Witt, et al. "Establishing traceability of photometric absorbance values for accurate measurements of the haemoglobin concentration in blood.", Metrologia 50 (2013) 539-548.

Putzu, et al., "Leucocyte classification for leukaemia detection using image processing techniques.", Artificial Intelligence in Medicine, vol. 63, No. 3, Nov. 1, 2014, pp. 1-31.

Varga, et al., "An automated scoring procedure for the micronucleus test by image analysis", Mutagenesis vol. 19 No. 5 pp. 391--397, 2004.

Ran, Qiong et al. "Spatial-spectral blood cell classification with microscopic hyperspectral imagery", Proc. SPIE 10461, AOPC 2017: Optical Spectroscopy and Imaging, 1046102 (Oct. 24, 2017) (12 pages total).

Omucheni et al. "Application of principal component analysis to multispectral-multimodal optical image analysis for malaria diagnostics", Malaria Journal 2014, 13:485 http://www.malariajournal.com/content/13/1/485 (11 pages total).

Ben-Suliman—2018—"Computerized Counting-Based System for Acute Lymphoblastic Leukemia Detection in Microscopic Blood Images" 27th International Conference on Artificial Neural Networks, Rhodes, Greece, Oct. 4-7, 2018, Proceedings, Part II, pp. 167-178.

An Office Action dated Dec. 8, 2020 for Japanese Patent Application No. 2018/512961.

An Examination Report dated Dec. 7, 2020 for Australian Patent Application No. 2016322966.

An Office Action dated Jan. 11, 2021 for U.S. Appl. No. 16/098,893.

An Examination Report dated Apr. 29, 2021 for Australian Patent Application No. 2016322966.

International Search Report issued for PCT Application No. PCT/IB2020/059924 dated Mar. 22, 2021.

International Search Report issued for PCT Application No. PCT/IB2020/059925 dated Mar. 26, 2021.

Invitation to pay fees and Partial Search Report issued for PCT Application No. PCT/IB2020/059924 dated Jan. 28, 2021.

Invitation to pay fees and Partial Search Report issued for PCT Application No. PCT/IB2020/059925 dated Feb. 4, 2021.

A Japanese Office Action dated Mar. 30, 2021, which issued during the prosecution of Application No. 2018/558180.

An Office Action dated Mar. 9, 2021 for U.S. Appl. No. 16/088,321.

An Office Action dated Jan. 29, 2021 for U.S. Appl. No. 16/099,270.

An Office Action dated Aug. 24, 2020 for U.S. Appl. No. 16/098,893.

A Chinese Office Action and dated May 22, 2020. which issued during the prosecution of Chinese Application No. 201680053431.1.

A Restriction Requirement issued by the USPTO dated Aug. 24, 2020 for U.S. Appl. No. 16/088,321.

A European Examination Report issued for European Patent Application No. 17728277.9 dated Dec. 23, 2021.

A Non-Final Office Action dated May 26, 2022 which issued during the prosecution of U.S. Appl. No. 17/083,775.

An Office Action dated Feb. 16, 2022 which issued during the prosecution of U.S. Appl. No. 16/088,321.

An Office Action dated May 31, 2022 which issued during the prosecution of U.S. Appl. No. 17/083,659.

An Office Action dated May 6, 2022 which issued during the prosecution of U.S. Appl. No. 16/763,810.

Examination Report issued by the Indian Patent Office dated Jun. 28, 2022 in Indian Patent Application No. 202047019700.

Notice of Allowance dated Nov. 10, 2021, which issued during the prosecution of U.S. Appl. No. 16/851,686.

Notice of Allowance dated Jan. 21, 2022, which issued during the prosecution of U.S. Appl. No. 16/098,893.

Notice of Allowance dated Nov. 5, 2021, which issued during the prosecution of U.S. Appl. No. 16/851,410.

Supplemental Notice of Allowance dated Nov. 12, 2021, which issued during the prosecution of U.S. Appl. No. 16/851,686.

An Extended European Search Report issued for European Patent Application No. 21164814.2 dated Jun. 9, 2021.

Third Office Action dated Jul. 12, 2021 which issued during the prosecution of Chinese Patent Application No. 201680053431.1.

Non-Final Office Action dated Jul. 27, 2021, which issued during the prosecution of U.S. Appl. No. 16/851,686.

Non-Final Office Action dated Aug. 19, 2021, which issued during the prosecution of U.S. Appl. No. 16/098,893.

(56) References Cited

OTHER PUBLICATIONS

Non-Final Office Action dated Sep. 1, 2021 which issued during the prosecution of U.S. Appl. No. 16/088,321.
First Office Action dated Aug. 4, 2021 which issued during the prosecution of Chinese Patent Application No. 201780027908.3.
An Examination Report dated Mar. 4, 2021 which issued during the prosecution of Indian Patent Application No. 201817036130.
An Examination Report dated May 5, 2021 which issued during the prosecution of Indian Patent Application No. 201817012117.
Notice of Allowance dated Aug. 3, 2021, which issued during the prosecution of U.S. Appl. No. 16/851,410.
An International Search Report and Written Opinion for Application No. PCT/IB2020/061731 dated Feb. 10, 2021.
Invitation to pay fees and Partial Search Report issued for PCT Application No. PCT/IB2020/061732 dated Mar. 10, 2021.
Invitation to pay fees and Partial Search Report issued for PCT Application No. PCT/IB2020/061736 dated Mar. 12, 2021.
Invitation to pay fees and Partial Search Report issued for PCT Application No. PCT/IB2020/061728 dated Mar. 15, 2021.
International Search Report issued for PCT Application No. PCT/IB2020/061724 dated Mar. 10, 2021.
An International Search Report and Written Opinion for PCT Application No. PCT/IB2020/061732 dated May 7, 2021.
International Search Report and Written Opinion for PCT Application No. PCT/IB2020/061728 dated May 7, 2021.
International Search Report and Written Opinion for PCT Application No. PCT/IB2020/061736 dated May 3, 2021.
Non-Final Office Action dated Jun. 17, 2021 which issued during the prosecution of U.S. Appl. No. 16/851,410.
A Final Office Action dated Jun. 17, 2021 which issued during the prosecution of U.S. Appl. No. 16/088,321.
Notice of Allowance dated May 19, 2021 which issued during the prosecution of U.S. Appl. No. 16/099,270.
A Restriction Requirement issued by the USPTO dated Oct. 19, 2020 for U.S. Appl. No. 16/099,270.
Non-Final Office Action dated Oct. 6, 2021, which issued during the prosecution of U.S. Appl. No. 17/063,320.
A Final Office Action dated Jul. 29, 2019 which issued during the prosecution of U.S. Appl. No. 14/914,329 (SDX024-CAT-2).
A Restriction Requirement issued by the USPTO dated Aug. 24, 2020 for U.S. Appl. No. 16/088,321. (SDX049-CAT-3).
An Office Action issued by the USPTO dated Aug. 24, 2020 for U.S. Appl. No. 16/098,893. (SDX063-CAT-3).
An Office Action dated Dec. 18, 2019, which issued during the prosecution of U.S. Appl. No. 15/174,490 (SDX004-CAT-1).
Bovik, Alan C., et. "The Essential Guide to Image Processing", Chapter 27, "Computer Assisted Microscopy", pp. 777-831; Academic Press, 2009.
A European Examination Report dated Dec. 9, 2019. which issued during the prosecution of Applicant's European App No. 16782094.3.
Notice of Allowance dated Mar. 2, 2020, which issued during the prosecution of U.S. Appl. No. 16/657,473.
A European Examination Report dated Feb. 1, 2019. which issued during the prosecution of Applicant's European App No. 17717000.8.
A European Examination Report dated Sep. 3, 2019. which issued during the prosecution of Applicant's European App No. 17717000.8.
A European Examination Report dated Apr. 8, 2020. which issued during the prosecution of Applicant's European App No. 17717000.8.
A European Examination Report dated Apr. 6, 2020. which issued during the prosecution of Applicant's European App No. 17726036.1.
A European Examination Report dated Feb. 11, 2020. which issued during the prosecution of Applicant's European App No. 17728277.9.

Steven S.S. Poon, et al., "Automated Image Detection and Segmentation in Blood Smears", Cytometry, 1992, pp. 766-774, vol. 13 (9 pages total).
John F. Brenner, et al., "An Automated Microscope for Cytologic Research a Preliminary Evaluation", The Journal of Histochemistry and Cytochemistry, 1976, pp. 100-111, vol. 24, No. 1 (12 pages total).
S A H Jahanmehr, et al., "Simple Technique for Fluorescence Staining of Blood Cells with Acridine Orange", Journal of Clinical Pathology, Feb. 12, 1987, pp. 926-929 (4 pages total).
Anne Fohlen-Walter, PhD, et al., "Laboratory Identification of Cryoglobulinemia From Automated Blood Cell Counts, Fresh Blood Samples, and Blood Films", American Society for Clinical Pathology, 2002, pp. 606-614, vol. 117 (9 pages total).
Caicai Wu, et al., "Feasibility study of the spectroscopic measurement of oxyhemoglobin using whole blood without pre-treatment", The Analyst, Mar. 1998, pp. 477-481, vol. 123 (5 pages total).
C. Briggs, et al., "Continuing developments with the automated platelet count", Blackwell Publishing Ltd, International Journal of Laboratory Hematology, Jan. 18, 2007, pp. 77-91, vol. 29 (15 pages total).
International Search Report in International Application No. PCT/IB2018/058861, dated Apr. 8, 2019.
Written Opinion in International Application No. PCT/IB2018/058861, dated Apr. 8, 2019.
Office Action dated Apr. 4, 2019, which issued during the prosecution of U.S. Appl. No. 14/914,329.
Notice of Allowance dated Mar. 20, 2019, which issued during the prosecution of U.S. Appl. No. 15/506,997.
Office Action dated Jun. 5, 2019, which issued during the prosecution of U.S. Appl. No. 15/174,490.
Office Action dated Jun. 4, 2019, which issued during the prosecution of U.S. Appl. No. 14/369,251.
Bieler, s., et al., "Improved detection of Trypanosoma brucei by lysis of red blood cells, concentration and LED fluorescence microscopy", Acta Tropica, vol. 121, Issue 2, 2012, pp. 135-140.
Chiodini, P.L., et al., "Rapid diagnosis of malaria by fluorescence microscopy", The Lancet, vol. 337, 1991, pp. 624-625.
Communication dated Apr. 2, 2015 from the United States Patent and Trademark Office in U.S. Appl. No. 13/338,291.
Communication dated Feb. 22, 2018 from the United States Patent and Trademark Office in U.S. Appl. No. 14/369,251.
Communication dated Dec. 24, 2018 from the Intellectual Property India Patent Office in application No. 3592/MUMNP/2015.
Communication dated Jan. 28, 2019 from the United States Patent and Trademark Office in U.S. Appl. No. 15/174,490.
Communication dated Jan. 31, 2019 from the Intellectual Property India Patent Office in application No. 5069/DELNP/2012.
Communication dated Mar. 23, 2018 from the Intellectual Property India Patent Office in application 4263/DELNP/2014.
Communication dated Nov. 16, 2018 from the United States Patent and Trademark Office in U.S. Appl. No. 14/914,329.
Communication dated Sep. 25, 2015 from the United States Patent and Trademark Office in U.S. Appl. No. 13/338,291.
Communication dated Oct. 29, 2014 from the United States Patent and Trademark Office in U.S. Appl. No. 13/338,291.
Diagnostic Procedures, "Blood Specimens: Microscopic Examination", 2009, 2 pages, http://mcdinternational.org/trainings/malaria/english/dpdx5/HTML/Frames/DiagnosticProcedures/body_dp_bloodexamin.
Gallo, V., et al.,"Simultaneous determination of phagocytosis of Plasmodium falciparum-parasitized and non-parasitized red blood cells by flow cytometry", Malaria Journal, vol. 11, No. 428, 2012, pp. 1-11.
International Search Report and Written Opinion, dated Aug. 8, 2017 from the International Bureau in counterpart International application No. PCT/IL2017/050523.
International Search Report and Written Opinion, dated May 18, 2017 from the International Bureau in counterpart International application No. PCT/IL2017/050363.
International Search Report and Written Opinion, dated Aug. 30, 2017 from the International Bureau in counterpart International application No. PCT/IL2017/050526.

(56) References Cited

OTHER PUBLICATIONS

International Search Report and Written Opinion, dated Jul. 27, 2012 from the International Bureau in counterpart International application No. PCT/IL2011/000973.
Jager, M.M., et al., "Five-minute Giemsa stain for rapid detection of malaria parasites in blood smears", Tropical Doctor, vol. 41, 2011, pp. 33-35.
Joannya, F., et. al., "In Vitro Activity of Fluorescent Dyes against Asexual Blood Stages of Plasmodium falciparum", Abtimicrobial Agents and Chemotherapy, vol. 56, No. 11, 2012, pp. 5982-5985.
Kumar, A., et al., "Enhanced Identification of Malarial Infected Objects using Otsu Algorithm from Thin Smear Digital Images", International Journal of Latest Research in Science and Technology, vol. 1, Issue 2, 2012, pp. 159-163.
Le, M.-T., et al., "A novel semi-automatic image processing approach to determine Plasmodium falciparum parasitemia in Giemsa-stained thin blood smears", BioMed Central Cell Biology, 2008, vol. 9, No. 15, pp. 1-12.
Garcia, et al. "M15-A Laboratory Diagnosis of Blood-borne Parasitic Diseases; Approved Guideline", Clinical and Laboratory Standards Institute, vol. 20, No. 12, Jun. 2000 (13 pages).
Mendiratta, DK, et al., "Evaluation of Different Methods for Diagnosis of P. Falciparum Malaria", Indian Journal of Medical Microbiology, 2006, vol. 24, No. 1, pp. 49-51.
Moon, S., et al., "An Image Analysis Algorithm for Malaria Parasite Stage Classification and Viability Quantification", PLoS ONE, vol. 8, Issue 4, e61812, Apr. 2013, pp. 1-12.
Notice of Allowance dated Jan. 19, 2016, from the United States Patent and Trademark Office in U.S. Appl. No. 13/338,291.
Notice of Allowance dated Mar. 10, 2016 from the United States Patent and Trademark Office in U.S. Appl. No. 13/338,291.
Pasini, E., et. al., "A novel live-dead staining methodology to study malaria parasite viability", Malaria Journal, vol. 12, No. 190, 2013, pp. 1-10.
Piruska, A., et al., "The autofluorescence of plastic materials and chips measured under laser irradiation", Lab on a Chip, vol. 5, 2005, pp. 1348-1354 (7 pages).
Sheikh, H., et al., "Blood Cell Identification Using Neural Networks", Proceedings of the IEEE 2nd Annual Northeast Bioengineering Conference, Mar. 1996, 2 pages.
Tek, F. et al., "Parasite detection and identification for automated thin blood film malaria diagnosis", Computer Vision and Image Understanding, vol. 114, Issue 1, 2010, pp. 21-32.
Unitaid "Malaria Diagnostics Technology and Market Landscape", 2nd Edition, Jul. 2014, pp. 1-140 (148 pages).
Wissing, et al., "Illumination of the Malaria Parasite *Plasmodium falciparum* Alters Intracellular pH", The Journal of Biological Chemistry, vol. 277, No. 40, Issue of Oct. 4, pp. 37747-37755, 2002, (10 pages).
Wright, J., "A Rapid Method For The Differential Staining Of Blood Films And Malarial Parasites", Journal of Medical Research, vol. 7, No. 1, 1902, pp. 138-144 (7 pages).
Yao, LN., et al., "Pathogen Identification and Clinical Diagnosis for One Case Infected with Babesia", Chinese Journal of Parasitology Parasitic Diseases, vol. 30, No. 2, Apr. 2012, pp. 118-121 (4 pages).
An Office Action dated Jan. 10, 2018, which issued during the prosecution of U.S. Appl. No. 15/083,610.
Matcher, S. J., M. Cope, and D. T. Delpy. "Use of the water absorption spectrum to quantify tissue chromophore concentration changes in near-infrared spectroscopy." Physics in medicine and biology 38.1 (19934): 177-196.
Rappaz, Benjamin, et al. "Comparative study of human erythrocytes by digital holographic microscopy, confocal microscopy, and impedance volume analyzer." Cytometry Part A 73.10 (2008): 895-903.
Ross, Nicholas E., et al. "Automated image processing method for the diagnosis and classification of malaria on thin blood smears." Medical and Biological Engineering and Computing 44.5 (2006): 427-436.

Houri-Yafin, A., et al. "An enhanced computer vision platform for clinical diagnosis of malaria." Malar Control Elimin 5.138.10 (2016): 4172.
Ahirwar, Neetu, Sapnojit Pattnaik, and Bibhudendra Acharya. "Advanced image analysis based system for automatic detection and classification of malarial parasite in blood images." International Journal of Information Technology and Knowledge Management 5.1 (2012): 59-64.
An Office Action dated Aug. 4, 2017, which issued during the prosecution of U.S. Appl. No. 14/369,251.
An Office Action dated Jun. 13, 2017, which issued during the prosecution of U.S. Appl. No. 14/285,672.
An Office Action dated Jul. 11, 2017, which issued during the prosecution of U.S. Appl. No. 15/174,490.
Osibote, O. A., et al. "Automated focusing in bright-field microscopy for tuberculosis detection." Journal of microscopy 240.2 (2010): 155-163.
Shen, Feimo, Louis Hodgson, and Klaus Hahn. "Digital autofocus methods for automated microscopy." Methods in enzymology 414 (2006): 620-632.
Wu, Qiang, Fatima Merchant, and Kenneth Castleman. Microscope image processing. Chapter 16, "Autofocusing", pp. 441-467, Academic press, 2010.
Purwar, Yashasvi, et al. "Automated and unsupervised detection of malarial parasites in microscopic images." Malaria journal 10.1 (2011): 364, pp. 1-10 (11 pages).
Frean, John. "Microscopic determination of malaria parasite load: role of image analysis." Microscopy: Science, technology. Applications, and Education (2010): 862-866.
Price, Jeffrey H., and David A. Gough. "Comparison of phase-contrast and fluorescence digital autofocus for scanning microscopy." Cytometry 16.4 (1994): 283-297.
Vink, J. P., etal. "An automatic vision based malaria diagnosis system." Journal of microscopy 250.3(2013): 166-178.
Chong, Shau Poh, Shilpa Pant, and Nanguang Chen. "Line-scan focal modulation microscopy for rapid imaging of thick biological specimens." S PIE/OS A/IEEE Asia Communications and Photonics. International Society for Optics and Photonics, 2011.
Yang, Ming, and Li Luo. "A rapid auto-focus method in automatic microscope." Signal Processing, 2008, ICSP 2008. 9th International Conference on. IEEE, 2008.
Anand, A., et al. "Automatic identification of malaria-infected RBC with digital holographic microscopy using correlation algorithms." Photonics Journal, IEEE 4.5 (2012): 1456-1464.
Ortyn, William E., et al. "Extended depth of field imaging for high speed cell analysis." Cytometry Part A 71.4 (2007): 215-231.
Sun, Yu, Stefan Duthaler, and Bradley J. Nelson. "Autofocusing algorithm selection in computer microscopy." Intelligent Robots and Systems, 2005, (IROS 2005). 2005 IEEE/RSJ International Conference on. IEEE, 2005.
Keiser, J., et al. "Acridine Orange for malaria diagnosis: its diagnostic performance, its promotion and implementation in Tanzania, and the implications for malaria control." Annals of tropical medicine and parasitology, 96.7 (2002): 643-654.
Shute, G. T., and T. M. Sodeman. "Identification of malaria parasites by fluorescence microscopy and acridine orange staining." Bulletin of the World Health Organization, 48.5 (1973): 591.
Kawamoto, Fumihiko, "Rapid diagnosis of malaria by fluorescence microscopy with light microscope and interference filter". The Lancet, vol. 337, pp. 200-202, Jan. 26, 1991.
Emma Eriksson et al: "Automated focusing of nuclei for time lapse experiments on single cells using holographic optical tweezers", Optics Express, vol. 17, No. 7, Mar. 24, 2009, pp. 5585-5594.
Kawamoto, F. and P. F. Billingsley. "Rapid diagnosis of malaria by fluorescence microscopy." Parasitology today 8.2 (1992): 69-71.
An International Search Report and a Written Opinion both dated Jan. 15, 2016, which issued during the prosecution of Applicant's PCT/IL2015/050864.
Tek, F. Boray, Andrew G. Dempster, and Izzet Kale. "Computer vision for microscopy diagnosis of malaria." Malaria Journal 8.1 (2009): 153, pp. 1-14.

(56) References Cited

OTHER PUBLICATIONS

Merchant, et al. "The essential guide to image processing", chapter 27, "Computer assisted Microscopy", pp. 777-831. Academic Press, 2009.
Thung, Ferdian, and Iping Supriana Suwardi. "Blood parasite identification using feature based recognition." Electrical Engineering and Informatics (ICEEI), 2011 International Conference on. IEEE, 2011.
Bacus, J.W., 1985. Cytometric approaches to red blood cells. Pure and Applied Chemistry, 57(4), pp. 593-598.
Centers for Disease Control and Prevention. "DPDx—Laboratory Identification of Parasitic Diseases of Public Health Concern", <http://www.cdc.gov/dpdx/diagnosticProcedures/blood/microexam.html>, Nov. 29, 2013.
An International Search Report and a Written Opinion both dated Feb. 12. 2015, which issued during the prosecution of Applicant's PCT/IL2014/050770.
U.S. Appl. No. 61/870,106, filed Aug. 26, 2013.
The use of fluorescence enhancement to improve the microscopic diagnosis of falciparum malaria Malaria Journal 2007, 6:89 http://www.malariajonmal.com/content/6/1/89, Rebecca Guy, Paul Liu, Peter Pennefather and Ian Crandall (Jul. 6, 2007).
Leif, "Methods for Preparing Sorted Cells as Monolayer Specimens", Springer Lab Manuals, Section 7—Chapter 5, pp. 592-619, (2000).
An Office Action dated Oct. 5, 2016, which issued during the prosecution of U.S. Appl. No. 14/285,672.
Groen F C A et al: "A Comparison of Different Focus Functions for Use in Autofocus Algorithms", Cytometry, Alan Liss, New York, US, vol. 6, No. 2, Mar. 1, 1985 (Mar. 1, 1985), pp. 81-91Groen F C A et al: "A Comparison of Different Focus Functions for Use in Autofocus Algorithms", Cytometry, Alan Liss, New York, US, vol. 6, No. 2, Mar. 1, 1985 (Mar. 1, 1985), pp. 81-91.
Andrew Gordon et al: "Supplementary Note to Gordon et al: "Single-cell quantification of molecules . . . "". Nature Methods, Jan. 21, 2007, pp. 1-35.
Andrew Gordon et al: "Single-cell quantification of molecules and rates using open-source microscope-based cytometry", HHS Public Access Author Manuscript, vol. 4, No. 2, Jan. 21, 2007, pp. 175-181.
European Search Report dated Dec. 14, 2016. which issued during the prosecution of Applicant's European App No. 14800352.8.
An International Search Report and a Written Opinion both dated Sep. 29. 2014. which issued during the prosecution of Applicant's PCT/IL2014/050423.
An International Search Report and a Written Opinion both dated Apr. 18. 2013, which issued during the prosecution of Applicant's PCT/IL2012/050556.
An International Search Report and a Written Opinion both dated Oct. 30. 2014, which issued during the prosecution of Applicant's PCT/IL2014/050585.
Notice of Allowance dated Jan. 11. 2016, which issued during the prosecution of U.S. Appl. No. 14/440,864.
High-content live cell imaging with RNA probes: advancements in high-throughput antimalarial drug discovery BMC Cell Biology 2009, 10:45 www.biomedcentral.com/1471-2121/10/45 Serena Cervantes, Jacques Prudhomme, David Carter, Krishna G Gopi, Qian Li, Young-Tae Chang and Karine G Le Roch (Jun. 10, 2009).
Plasmodium yoelii: A differential fluorescent technique using Acridine Orange to identify infected erythrocytes and reticulocytes in Duffy knockout mouse. Experimental Parasitology vol. 110, Issue 1, May 2005, pp. 80-87. <http://www.sciencedirect.com/science/article/_pii/S001448940500038X >: Lili Xu, Asok Chaudhuri (May 31, 2005).
Notice of Allowance dated Dec. 30, 2015, which issued during the prosecution of U.S. Appl. No. 14/440,864.
Zahniser et al., Automated Slide Preparation System for the Clinical Laboratory, Cytometry, vol. 26, No. 10, pp. 30-64, (1996).
Moody, "Rapid Diagnostic Tests for Malaria Parasites", Clinical Microbiology Reviews, vol. 15, No. 1, pp. 66-78, (2002).

Knesel, "Roche Image Analysis Systems, Inc.", Acta Cytologica, vol. 40, pp. 60-66, (1996).
Life Technologies Corporation, "Counting blood cells with Countess Automated Cell Counter" pdf, four pages, (2009).
An Office Action dated Mar. 2, 2017, which issued during the prosecution of U.S. Appl. No. 14/369,251.
An International Search Report and a Written Opinion both dated Jan. 23, 2017, which issued during the prosecution of Applicant's PCT/IL2016/051025.
European Search Report dated Mar. 23, 2017. which issued during the prosecution of Applicant's European App No. 14839661.7.
An International Preliminary Report on Patentability dated Feb. 28, 2017, which issued during the prosecution of Applicant's PCT/IL2015/050864.
Roma, P. M. S., et al. "Total three-dimensional imaging of phase objects using defocusing microscopy: Application to red blood cells." Applied Physics Letters 104.25 (2014): 251107.
Agero, U., Mesquita, L.G., Neves, B.R.A., Gazzinelli, R.T. and Mesquita, O.N., 2004. Defocusing microscopy. Microscopy research and technique, 65(3), pp. 159-165.
Yazdanfar, S., Kenny, K.B., Tasimi, K., Corwin, A.D., Dixon, E.L. and Filkins, R.J., 2008. Simple and robust image-based autofocusing for digital microscopy. Optics express, 16(12), pp. 8670-8677.
Bravo-Zanoguera, M.E., Laris, C.A., Nguyen, L.K., Oliva, M. and Price, J.H., 2007. Dynamic autofocus for continuous-scanning time-delay-and-integration image acquisition in automated microscopy. Journal of biomedical optics, 12(3), pp. 034011-1 to 034011-16.
U.S. Appl. No. 62/042,388, filed Aug. 27, 2014.
Communication dated Jun. 15, 2018 from the United States Patent and Trademark Office in U.S. Appl. No. 14/369,251.
Communication dated Jun. 29, 2018 from the United States Patent and Trademark Office in U.S. Appl. No. 15/174,490.
An Office Action dated Jul. 12, 2022, which issued during the prosecution of U.S. Appl. No. 16/088,321.
An Office Action dated Aug. 2, 2022, which issued during the prosecution of Japanese Patent Application No. 2021-145455.
An Examination Report dated Aug. 25, 2022, which issued during the prosecution of Australian Patent Application No. 2017263807.
An Office Action dated Aug. 30, 2022 which issued during the prosecution of Japanese Patent Application No. 2020-526176.
An Office Action dated Sep. 13, 2022 which issued during the prosecution of Japanese Patent Application No. 2021-157849.
Hideto Miura, "How to regard as how to consider the poikilocyte in urine an erroneous decision factor", Modern Medical Laboratory, Sep. 1, 2002, vol. 30, No. 9, pp. 862-864 (6 pages total).
Jun Hashimoto, "Morphological Studies of Urinary Red Blood Cells in Renal and Urinary Tract Disorders (II) Use of Wright's Stain in Differential Diagnosis between Renal and Urinary Tract Disorders" Kawasaki Medical Congress Magazine, Mar. 1989, vol. 15, No. 1, pp. 94-101 (9 pages total).
D F Birch et al., "The research on the differential diagnosis of the kidney urinary tract obstacle by glomerular or non-glomerular", Lancet, Oct. 20, 1979, vol. 2, No. 8147, pp. 845-846 (3 pages total).
A First Examination Report dated Sep. 19, 2022, which issued during the prosecution of Indian Patent Application No. 201817040226.
An Office Action dated Oct. 3, 2022 which issued during the prosecution of U.S. Appl. No. 16/763,810.
An Office Action dated Oct. 25, 2022 which issued during the prosecution of Canadian Application No. 2,998,829 (SDX044).
An Office Action dated Oct. 5, 2022 which issued during the prosecution of Brazilian Application No. 112018005099-7.
An Office Action dated Nov. 25, 2022 which issued during the prosecution of Brazilian Application No. 122020017765-9.
An Office Action dated Dec. 9, 2022 which issued during the prosecution of U.S. Appl. No. 17/083,647.
An Office Action dated Dec. 28, 2022 which issued during the prosecution of Russian Patent Application No. 2022112399.
An Office Action dated Dec. 28, 2022 which issued during the prosecution of Russian Patent Application No. 2022112393.
An Office Action dated Jan. 6, 2023 which issued during the prosecution of U.S. Appl. No. 17/063,320.

(56) References Cited

OTHER PUBLICATIONS

An Office Action dated Sep. 2, 2022 which issued during the prosecution of U.S. Appl. No. 17/063,320.
An Office Action dated Jan. 5, 2023 which issued during the prosecution of Chinese Patent Application No. 201880079888.9.
An Examination Report dated Jan. 23, 2023, which issued during the prosecution of Australian Patent Application No. 2022200112.
An Office Action dated Jan. 19, 2023 which issued during the prosecution of U.S. Appl. No. 17/490,767
Office Action dated Mar. 17, 2023 issued in U.S. Appl. No. 17/083,647.
A. K. Sawhney et al., "Erythrocyte Alterations Induced by Malathion in Channa punctatus (Bloch)", Bull. Environ. Contam. Toxicol, 2000, vol. 64, pp. 398-405 (9 pages total).
An Extended European Search Report which dated Mar. 20, 2023 for Application No. 22209948.3.
An Office Action dated Feb. 22, 2023 which issued during the prosecution of Canadian Application No. 3,081,669.
An Office Action dated Mar. 2, 2023 which issued during the prosecution of Canadian Application No. 3,018,536.
An Office Action dated Mar. 27, 2023 which issued during the prosecution of Brazilian Application No. 122020017765-9.
An Office Action dated Mar. 27, 2023 which issued during the prosecution of U.S. Appl. No. 16/763,810.
An Office Action dated Mar. 3, 2022, which issued during the prosecution of U.S. Appl. No. 17/063,320.
An Office Action dated Mar. 7, 2023 which issued during the prosecution of Japanese Application No. JP 2021-157849.
Masafumi ONODERA, "Organ Derangement", Medicina, Sep. 9, 2005, vol. 42, No. 9, pp. 1582-1584 (6 p. total).
Notice of Allowance issued for U.S. Appl. No. 16/088,321 on Apr. 12, 2023.
Olga V. Tyulina et al., "Erythrocyte and plasma protein modification in alcoholism: A possible role of acetaldehyde", Biochimica et Biophyisca, 2006, vol. 1762, pp. 558-563 (7 p. total).
Taihei TAKAKUSAKI, "Shape Change of Red Cell Ghost and ATP", The KITAKANTO Medical Journal, 1960, vol. 10, Issue 4, pp. 522-531 (11 p. total).
Tetsuya HIROTA et al., Kusanon AR Poisoning Complicated by Heinz Body Hemolytic Anemia, Japanese Association for Acute Medicine Magazine, vol. 12, No. 12, Dec. 15, 2001, pp. 749-754 (1 p. total).
An Office Action dated Jun. 8, 2023 which issued during the prosecution of Canadian Application No. 3,160,692.
An Office Action dated Jun. 9, 2023 which issued during the prosecution of Canadian Application No. 3,160,688.
An Office Action dated Jun. 22, 2023 which issued during the prosecution of Canadian Application No. 3,160,697.
An Office Action mailed on Jul. 3, 2023 which issued during the prosecution of U.S. Appl. No. 17/568,858.
An Office Action dated Jul. 12, 2023 which issued during the prosecution of Canadian Application No. 3,155,820.
An Office Action dated Jul. 17, 2023 which issued during the prosecution of Canadian Application No. 3,155,821.

\* cited by examiner

SAMPLE CARRIER FOR OPTICAL MEASUREMENTS

CROSS-REFERENCE TO RELATED APPLICATIONS

The present application is a continuation of U.S. Ser. No. 16/098,893 to Pollak (published as US 2019/0302099), which is a US national phase application of PCT Application No. PCT/IL2017/050523 to Pollak (published as WO 17/195205), filed May 11, 2017, which claims priority from U.S. Provisional Patent Application No. 62/334,521 to Pollak, filed May 11, 2016, entitled "Sample carrier for optical measurements."

The present application is related to PCT Application No. PCT/IL2017/050526 to Zait (published as WO 17/195208), filed May 11, 2017, entitled "Performing optical measurements on a sample," which claims priority from U.S. Provisional Patent Application No. 62/334,517 to Zait, filed May 11, 2016, entitled "Method and Apparatus for Estimating Dilution and Concentration."

Each of the above-referenced applications is incorporated herein by reference.

FIELD OF EMBODIMENTS OF THE INVENTION

Some applications of the presently disclosed subject matter relate generally to detecting components in a bodily sample, and in particular, to detecting components of a blood sample by performing optical measurements.

BACKGROUND

In some optics-based methods (e.g., diagnostic, and/or analytic methods), a property of a biological sample, such as a blood sample, is determined by performing an optical measurement. For example, the density of a component (e.g., a count of the component per unit volume) may be determined by counting the component within a microscopic image. Similarly, the concentration and/or density of a component may be measured by performing optical absorption, transmittance, fluorescence, and/or luminescence measurements upon the sample. Typically, the sample is placed into a sample carrier and the measurements are performed with respect to a portion of the sample that is contained within a chamber of the sample carrier. The measurements that are performed upon the portion of the sample that is contained within the chamber of the sample carrier are analyzed in order to determine a property of the sample.

SUMMARY OF EMBODIMENTS

In accordance with some applications of the present invention, a sample carrier includes one or more sample chambers configured to house a biological sample (such as, a blood sample). The one or more sample chambers typically define at least first and second regions thereof, and the height of the one or more sample chambers varies between the first and second regions in a predefined manner. For example, the height of the one or more sample chambers may vary between the first and second regions in a predefined stepped manner, or in a predefined gradual manner.

Typically, in order to perform optical analysis upon the sample, it is desirable to know the optical path length, the volume, and/or the thickness of the portion of the sample upon which the optical measurements were performed. Further typically, optical measurements are performed upon a portion of the sample disposed in a sample carrier that is defined by two or more opposing surfaces (e.g., a top surface and a bottom surface). In order to provide a desired level of precision for determining the parameter of the sample from the optical measurement, it is desirable for the two or more opposing surfaces to be separated by a distance that is correspondingly tightly set or tightly controlled. However, in some manufacture or assembly processes, the distance between the opposing surfaces may vary substantially.

As described hereinabove, in accordance with some applications of the present invention, one or more sample chambers of a sample carrier define at least first and second regions thereof, and the height of the one or more sample chambers varies between the first and second regions in a predefined manner. Typically, the sample carrier includes a first substrate the defines a first surface of the one or more sample chambers (e.g. the lower surface of the one or more sample chambers), and a second substrate that defines one or more surfaces of the one or more sample chambers that oppose the first surface (e.g. upper surfaces of the one or more sample chambers). The second substrate is shaped to define the one or more surfaces that oppose the first surface, such that one or more surfaces that oppose the first surface define the manner in which the height of the one or more sample chambers varies between the first and second regions (e.g., by defining two or more stepped surfaces that are parallel to the first surface, and oppose the first surface). Typically, manufacturing tolerances within a single substrate, and especially between nearby surfaces, are tighter than manufacturing tolerances on positioning between different substrates or even between opposing surfaces lying within the same substrate. Therefore, it is typically the case that by having a single substrate define the manner in which the height of the one or more sample chambers varies between the first and second regions, the height difference between the first and second regions is relatively precise.

Typically, a first optical measurement is performed upon a portion of the sample that is disposed within the first region of the one or more sample chambers, and a second optical measurement is performed upon a portion of the sample that is disposed within the second region. A property of the sample is determined by using a relationship between the first optical measurement, the second optical measurement, and the predefined variation in height between the first region and the second region.

For some applications, a sample carrier is provided that includes one or more sample chambers configured to house the sample. The one or more sample chambers define at least first and second regions thereof, and the height of the one or more sample chambers varies between the first and second regions. A biological sample is categorized and is placed into the one or more sample chambers of the sample carrier. Based upon the categorization of the biological sample, one of the regions of the sample carrier is selected upon which to perform optical measurements for measuring a given measurand. For example, if a sample, and/or a monolayer formed by the sample, has a relatively low density of red blood cells, then measurements may be performed upon a region of the sample carrier having a relatively great height, for example, such that there is a sufficient density of cells, and/or such that there is a sufficient density of cells within the monolayer, to provide statistically reliable data. Such measurements may include, for example, red blood cell density measurements, measurements of other cellular attributes, (such as counts of abnormal red blood cells, red blood cells that include intracellular bodies (e.g., pathogens, Howell-Jolly bodies), etc.), and/or hemoglobin concentration. Conversely, if a sample, and/or a monolayer formed by the sample, has a relatively high density of red blood cells, then such measurements may be performed upon a region of the sample carrier having a relatively low height, for example, such that there is a sufficient sparsity of cells, and/or such that there is a sufficient sparsity of cells within the monolayer formed by the sample, that the cells can be identified within microscopic images. For some applications, such methods are performed even without the difference in heights between the regions being precisely known.

There is therefore provided, in accordance with some applications of the present invention, apparatus for determining a property of a biological sample, the apparatus including:

a sample carrier that includes one or more sample chambers configured to house the sample, the one or more sample chambers defining at least first and second regions thereof, a height of the one or more sample chambers varying between the first and second regions in a predefined manner; and a computer processor configured to:

receive data relating to a first optical measurement that is performed upon a portion of the sample that is disposed within the first region, receive data relating to a second optical measurement that is performed upon a portion of the sample that is disposed within the second region, and determine the property of the sample by using a relationship between the first optical measurement, the second optical measurement, and the predefined variation in height between the first region and the second region.

In some applications, the height of the one or more sample chambers varies between the first and second regions in a predefined stepped manner.

In some applications, the height of the one or more sample chambers varies between the first and second regions in a predefined gradual manner.

In some applications, the computer processor is configured to receive the data relating to at least one of the first and second optical measurements by receiving imaging data from a microscope.

In some applications, the computer processor is configured to receive the data relating to at least one of the first and second optical measurements by receiving data relating to a parameter selected from the group consisting of: optical absorption, transmittance, fluorescence, and luminescence.

In some applications, the computer processor is configured to determine the property of the sample by determining a density of a component of the sample. In some applications, the computer processor is configured to determine the property of the sample by determining a concentration of a component of the sample. In some applications, the computer processor is configured to determine the property of the sample by determining a count of a component of the sample.

In some applications, the computer processor is configured to determine an absolute height of the one or more sample chambers within at least one of the first and second regions, using the relationship between the first optical measurement, the second optical measurement, and the predefined variation in height between the first region and the second region.

In some applications, the computer processor is configured to determine the property of the sample, by:

subtracting a parameter derived from the first optical measurement from a parameter derived from the second optical measurement; and determining the property of the sample, based upon a relationship between a result of the subtracting and the predefined variation in height between the first region and the second region.

In some applications, the computer processor is configured to determine the property of the sample, by:

dividing a parameter derived from the second optical measurement by a parameter derived from the first optical measurement; and determining the property of the sample, based upon a relationship between a result of the dividing and the predefined variation in height between the first region and the second region In some applications, the biological sample includes a blood sample, and the computer processor is configured to determine the property of the biological sample by determining a property of the blood sample. In some applications, the computer processor is configured to determine the property of the sample by determining a concentration of a given component within the blood sample. In some applications, the computer processor is configured to determine the property of the sample by determining a count of a given component within the blood sample. In some applications, the computer processor is configured to determine the property of the sample by determining a density of a given component within the blood sample.

In some applications, the one or more sample chambers define at least first, second, and third regions thereof, the height of the one or more sample chambers varying between each of the first, second, and third regions in a predefined manner.

In some applications, the computer processor is configured to:

receive data relating to a third optical measurement that is performed upon a portion of the sample that is disposed within the third region; and to determine the property of the sample, by performing statistical analysis with respect to the first, second, and third optical measurements, and the predefined variation in height between the first, second, and third regions.

In some applications, the computer processor is configured to:

determine a signal level of the biological sample, and based upon the determined signal level, select two out of the first, second, and third regions upon which to perform, respectively, the first and second optical measurements.

In some applications, the sample carrier includes:

a first substrate that defines a first surface; and a second substrate that defines one or more surfaces that oppose the first surface, and the second substrate is shaped to define the one or more surfaces that oppose the first surface, such that one or more surfaces that oppose the first surface define the manner in which the height of the one or more sample chambers varies between the first and second regions.

In some applications, the second substrate defines second and third surfaces, the second and third surfaces (a) opposing the first surface, (b) being parallel to the first surface, and (c) being stepped with respect to each other. In some applications, the second substrate that defines at least a second surface, the second surface (a) opposing the first surface, and (b) being non-parallel with respect to the first surface.

There is further provided, in accordance with some applications of the present invention, a method for determining a property of a biological sample, the method including:

providing a sample carrier, the sample carrier including one or more sample chambers configured to house the sample, the one or more sample chambers defining at least first and second regions thereof, a height of the one or more sample chambers varying between the first and second regions in a predefined manner;

placing the sample into the one or more sample chambers;

performing a first optical measurement upon a portion of the sample that is disposed within the first region;

performing a second optical measurement upon a portion of the sample that is disposed within the second region; and determining the property of the sample by using a relationship between the first optical measurement, the second optical measurement, and the predefined variation in height between the first region and the second region.

There is further provided, in accordance with some applications of the present invention, a computer software product, for use with a biological sample that is placed within a sample carrier that includes one or more sample chambers configured to house the sample, the one or more sample chambers defining at least first and second regions thereof, a height of the one or more sample chambers varying between the first and second regions, in a predefined manner, the computer software product including a non-transitory computer-readable medium in which program instructions are stored, which instructions, when read by a computer cause the computer to perform the steps of:

receiving data relating to a first optical measurement that is performed upon a portion of the sample that is disposed within the first region;

receiving data relating to a second optical measurement that is performed upon a portion of the sample that is disposed within the second region; and determining the property of the sample by using a relationship between the first optical measurement, the second optical measurement, and the predefined variation in height between the first region and the second region.

There is further provided, in accordance with some applications of the present invention, a method performing optical measurements on a biological sample, the method including:

providing a sample carrier that includes one or more sample chambers configured to house the sample, the one or more sample chambers defining at least first and second regions thereof, a height of the one or more sample chambers varying between the first and second regions;

categorizing the biological sample;

placing the sample into the one or more sample chambers; and based upon the categorization of the biological sample, selecting one of the first and second regions upon which to perform optical measurements for measuring a given measurand.

In some applications, categorizing the sample includes receiving an indication of the categorization of the sample. In some applications, categorizing the sample includes categorizing the sample based upon a density of one or more components within the sample. In some applications, categorizing the sample includes categorizing the sample based upon a surface density of one or more components within a monolayer formed by the sample. In some applications, categorizing the sample includes categorizing the sample based upon a concentration of one or more components within the sample. In some applications, categorizing the sample includes categorizing the sample based upon a count of one or more components within the sample. In some applications, categorizing the sample includes measuring a parameter of the sample selected from the group consisting of: optical absorption, transmittance, fluorescence, and luminescence, by performing a preliminary optical measurement upon the sample. In some applications, categorizing the sample includes performing microscopic imaging upon the sample.

In some applications, selecting one of the first and second regions upon which to perform optical measurements for measuring the given measurand includes selecting one of the first and second regions upon which to perform counting of a given component within the sample, by performing microscopic imaging upon the region. In some applications, selecting one of the first and second regions upon which to perform optical measurements for measuring the given measurand includes selecting one of the first and second regions upon which to measure a concentration of a given component within the sample, by measuring a parameter selected from the group consisting of: optical absorption, transmittance, fluorescence, and luminescence.

In some applications:

the one or more sample chambers define at least first, second, and third regions thereof, a height of the one or more sample chambers varying between each of the first, second, and third regions in a predefined manner; and based upon the identified property of the biological sample, selecting two out of the first, second, and third regions upon which to perform, respective, first and second optical measurements for measuring the given measurand.

In some applications, the method further includes:

performing the, respective, first and second optical measurements upon the selected two regions; and measuring the given measurand by using a relationship between the first optical measurement, the second optical measurement, and the predefined variation in height between the selected two regions.

In some applications, the biological sample includes a blood sample, and selecting one of the first and second regions upon which to perform optical measurements for measuring the given measurand includes selecting one of the first and second regions upon which to perform optical measurements for measuring a given measurand of the blood sample.

In some applications, selecting one of the first and second regions upon which to perform optical measurements for measuring the given measurand includes selecting one of the first and second regions upon which to measure a concentration of a given component within the blood sample, by measuring a parameter selected from the group consisting of: optical absorption, optical transmittance, fluorescence, and luminescence. In some applications, selecting one of the first and second regions upon which to perform optical measurements for measuring the given measurand includes selecting one of the first and second regions upon which to perform counting of a given component within the blood sample, by performing microscopic imaging upon the region.

There is further provided, in accordance with some applications of the present invention, apparatus for determining a property of a biological sample, the apparatus including:

a sample carrier that includes one or more sample chambers configured to house the sample, the one or more sample chambers defining at least first and second regions thereof, a height of the one or more sample chambers varying between the first and second regions; and a computer processor configured to:
categorize the biological sample, and
based upon the categorization of the biological sample, select one of the first and second regions upon which to perform optical measurements for measuring a given measurand of the biological sample.

There is further provided, in accordance with some applications of the present invention, a computer software product, for use with a biological sample that is placed within a sample carrier that includes one or more sample chambers configured to house the sample, the one or more sample chambers defining at least first and second regions thereof, a height of the one or more sample chambers varying between the first and second regions, the computer software product including a non-transitory computer-readable medium in which program instructions are stored, which instructions, when read by a computer cause the computer to perform the steps of:
categorizing the biological sample; and
based upon the categorization of the biological sample, selecting one of the first and second regions upon which to perform optical measurements for measuring a given measurand of the biological sample.

There is further provided, in accordance with some applications of the present invention, apparatus for performing optical measurements on a biological sample, the apparatus including:
a sample carrier that includes one or more sample chambers configured to house the sample,
the one or more sample chambers defining at least first, second, and third regions thereof, a height of the one or more sample chambers varying between each of the first, second, and third regions in a predefined manner.

There is further provided, in accordance with some applications of the present invention, a method for performing optical measurements on a biological sample, the method including:
providing a sample carrier, the sample carrier including one or more sample chambers configured to house the sample, the one or more sample chambers defining at least first and second regions thereof, a height of the one or more sample chambers varying between the first and second regions;
placing the sample into the one or more sample chambers;
measuring a first measurand, by performing a first optical measurement upon a portion of the sample that is disposed within the first region; and
measuring a second measurand, by performing a second optical measurement upon a portion of the sample that is disposed within the second region.

In some applications, the biological sample includes a blood sample, measuring the first measurand includes measuring a first measurand of the blood sample performing the first optical measurement upon a portion of the blood sample that is disposed within the first region, and measuring the second measurand includes measuring a second measurand of the blood sample by performing a second optical measurement upon a portion of the sample that is disposed within the second region.

In some applications, measuring the first measurand of the blood sample includes determining a count of a first component within the blood sample by performing microscopic imaging upon the portion of the sample that is disposed within the first region, and measuring the second measurand of the blood sample includes determining a count of a second component within the blood sample by performing microscopic imaging upon the portion of the sample that is disposed within the second region.

In some applications, measuring the first measurand of the blood sample includes measuring a concentration of a first component within the blood sample, by performing, upon the portion of the sample that is disposed within the first region, an optical measurement of a parameter selected from the group consisting of: optical absorption, transmittance, fluorescence, and luminescence. In some applications, measuring the second measurand of the blood sample includes measuring a concentration of a second component within the blood sample, by performing, upon the portion of the sample that is disposed within the second region, an optical measurement of a parameter selected from the group consisting of: optical absorption, transmittance, fluorescence, and luminescence. In some applications, measuring the second measurand of the blood sample includes determining a count of a second component within the blood sample by performing microscopic imaging upon the portion of the sample that is disposed within the second region.

There is further provided, in accordance with some applications of the present invention, apparatus for determining a property of a biological sample, the apparatus including:
a sample carrier that includes one or more sample chambers configured to house the sample, the one or more sample chambers defining at least first and second regions thereof, a height of the one or more sample chambers varying between the first and second regions; and
a computer processor configured to:
measure a first measurand, by receiving a first optical measurement performed upon a portion of the sample that is disposed within the first region; and
measure a second measurand, by receiving a second optical measurement performed upon a portion of the sample that is disposed within the second region.

There is further provided, in accordance with some applications of the present invention, a computer software product, for use with a biological sample that is placed within a sample carrier that includes one or more sample chambers configured to house the sample, the one or more sample chambers defining at least first and second regions thereof, a height of the one or more sample chambers varying between the first and second regions, the computer software product including a non-transitory computer-readable medium in which program instructions are stored, which instructions, when read by a computer cause the computer to perform the steps of:
measuring a first measurand, by receiving a first optical measurement performed upon a portion of the sample that is disposed within the first region; and
measuring a second measurand, by receiving a second optical measurement performed upon a portion of the sample that is disposed within the second region.

There is further provided, in accordance with some applications of the present invention, a method performing optical measurements on a biological sample, the method including:
providing a sample carrier that includes one or more sample chambers configured to house the sample, the one or more sample chambers defining at least first and second regions thereof, a height of the one or more sample chambers varying between the first and second regions;
categorizing a measurand of the biological sample that is to be measured;
placing the sample into the one or more sample chambers; and based upon the categorization of the measurand, selecting one of the first and second regions upon which to perform optical measurements for measuring the identified measurand.

In some applications, the biological sample includes a blood sample, categorizing the measurand of the biological sample that is to be measured includes categorizing a measurand of the blood sample that is to be measured.

In some applications, selecting one of the first and second regions upon which to perform optical measurements for measuring the identified measurand includes selecting one of the first and second regions upon which to measure a concentration of a given component within the blood sample, by measuring a parameter selected from the group consisting of: optical absorption, transmittance, fluorescence, and luminescence. In some applications, selecting one of the first and second regions upon which to perform optical measurements for measuring the identified measurand includes selecting one of the first and second regions upon which to perform microscopic imaging.

There is further provided, in accordance with some applications of the present invention, apparatus for determining a property of a biological sample, the apparatus including:

a sample carrier that includes one or more sample chambers configured to house the sample, the one or more sample chambers defining at least first and second regions thereof, a height of the one or more sample chambers varying between the first and second regions; and a computer processor configured to:
categorize a measurand of the biological sample that is to be measured, and
based upon the categorization of the measurand, select one of the first and second regions upon which to perform optical measurements for measuring the identified measurand.

There is further provided, in accordance with some applications of the present invention, a computer software product, for use with a biological sample that is placed within a sample carrier that includes one or more sample chambers configured to house the sample, the one or more sample chambers defining at least first and second regions thereof, a height of the one or more sample chambers varying between the first and second regions, the computer software product including a non-transitory computer-readable medium in which program instructions are stored, which instructions, when read by a computer cause the computer to perform the steps of:

categorizing a measurand of the biological sample that is to be measured; and based upon the categorization of the measurand, selecting one of the first and second regions upon which to perform optical measurements for measuring the identified measurand.

The present invention will be more fully understood from the following detailed description of embodiments thereof, taken together with the drawings, in which:

DETAILED DESCRIPTION OF EMBODIMENTS

Figure 1:
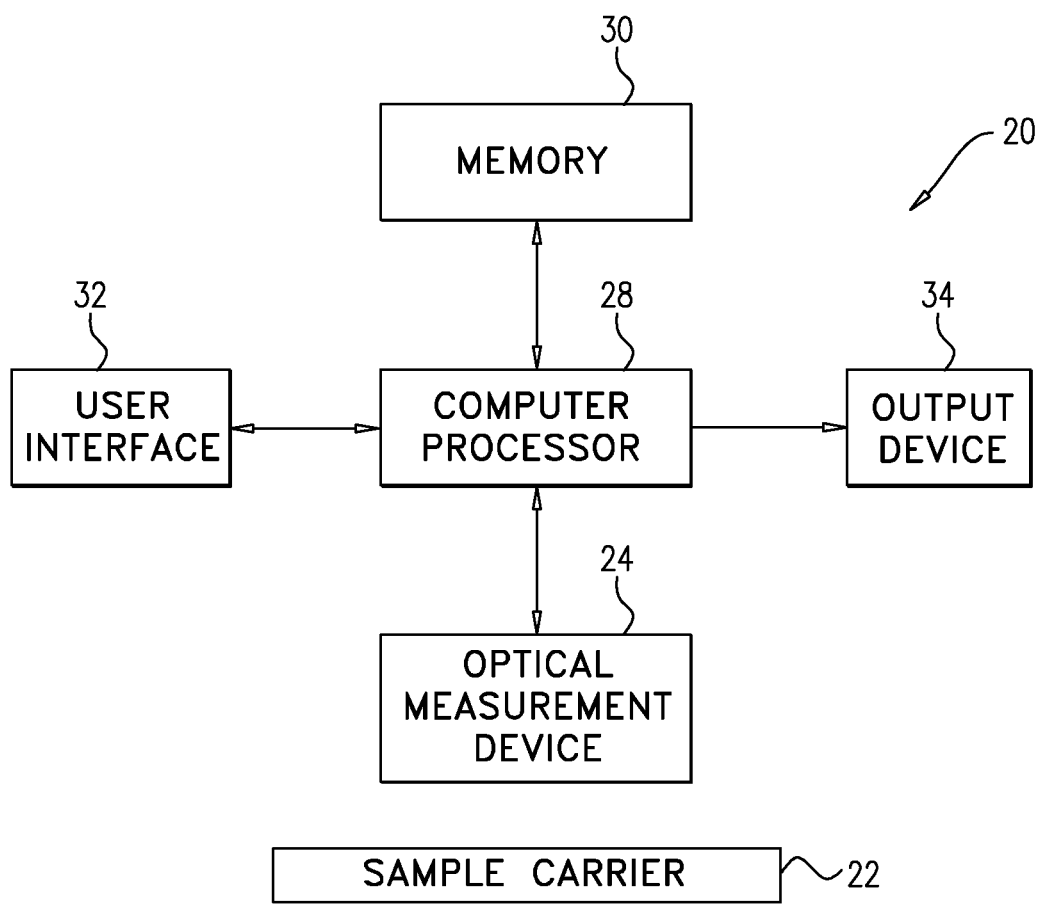
FIG. 1 is a block diagram showing components of a biological sample analysis system, in accordance some applications of the present invention.

Reference is now made to FIG. 1, which is block diagram showing components of a biological sample analysis system 20, in accordance some applications of the present invention. Typically, a biological sample (e.g., a blood sample) is placed into a sample carrier 22. While the sample is disposed in the sample carrier, optical measurements are performed upon the sample using one or more optical measurement devices 24. For example, the optical measurement devices may include a microscope (e.g., a digital microscope), a spectrophotometer, a photometer, a spectrometer, a camera, a spectral camera, a hyperspectral camera, a fluorometer, a spectrofluorometer, and/or a photodetector (such as a photodiode, a photoresistor, and/or a phototransistor). For some applications, the optical measurement devices include dedicated light sources (such as light emitting diodes, incandescent light sources, etc.) and/or optical elements for manipulating light collection and/or light emission (such as lenses, diffusers, filters, etc.). For some applications, a microscope system is used that is generally similar to the microscope system described in US 2014/0347459 to Greenfield, which is incorporated herein by reference.

A computer processor 28 typically receives and processes optical measurements that are performed by the optical measurement device. Further typically, the computer processor controls the acquisition of optical measurements that are performed by the one or more optical measurement devices. The computer processor communicates with a memory 30. A user (e.g., a laboratory technician) sends instructions to the computer processor via a user interface 32. For some applications, the user interface includes a keyboard, a mouse, a joystick, a touchscreen device (such as a smartphone or a tablet computer), a touchpad, a trackball, a voice-command interface, and/or other types of user interfaces that are known in the art. Typically, the computer processor generates an output via an output device 34. Further typically, the output device includes a display, such as a monitor, and the output includes an output that is displayed on the display. For some applications, the processor generates an output on a different type of visual, text, graphics, tactile, audio, and/or video output device, e.g., speakers, headphones, a smartphone, or a tablet computer. For some applications, user interface 32 acts as both an input interface and an output interface, i.e., it acts as an input/output interface. For some applications, the processor generates an output on a computer-readable medium (e.g., a non-transitory computer-readable medium), such as a disk, or a portable USB drive, and/or generates an output on a printer.

Figure 2:
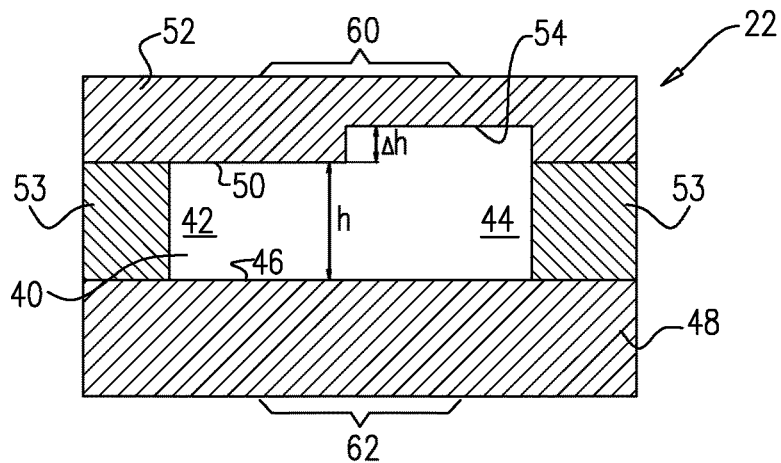
FIG. 2 is a schematic cross-sectional illustration of a sample carrier that defines a variation in height that is stepped, in accordance with some applications of the present invention.

Reference is now made to FIG. 2, which is a schematic cross-sectional illustration of sample carrier 22, in accordance with some applications of the present invention. The sample carrier defines one or more sample chambers 40, into which the sample is placed. The one or more sample chambers typically define at least a first region 42 (which is shallower) and a second region 44 (which is deeper), the height of the one or more sample chambers varying between the first and second regions in a predefined manner. For example, as shown in FIG. 2, the height of the one or more sample chambers varies between the first and second regions in a predefined stepped manner.

Typically, in order to perform optical analysis upon the sample, it is desirable to know the optical path length, the volume, and/or the thickness of the portion of the sample upon which the optical measurements were performed, as precisely as possible. Further typically, the optical measurements are performed upon a portion of the sample disposed in a sample carrier that is defined by two or more opposing surfaces. In order to provide the desired level of precision, it is desirable for the two or more opposing surfaces to be separated by a distance that is correspondingly tightly set or tightly controlled. However, in some manufacture or assembly processes, the distance between the opposing surfaces may vary substantially. For example, in some instances, two or more of the opposing surfaces lie in separate substrates that are bonded relative to each other during manufacture or assembly (e.g. using thermal bonding, solvent-assisted bonding, ultrasonic welding, laser welding, heat staking, adhesive, mechanical clamping and/or additional substrates).

For example, as shown in FIG. 2, the height of first region 42 of the sample chamber is defined by a lower surface 46 that is defined by a first substrate 48 (e.g., a glass or a plastic substrate) and by upper surface 50 that is defined by a second substrate 52 (e.g., a plastic substrate, such as an injection-molded plastic substrate). The first and second substrates are bonded to each other by an adhesive layer 53, e.g., a pressure-sensitive adhesive. Examples of the adhesive layer include an additional physical layer (such as a pressure-sensitive adhesive layer), a sandwich of pressure-sensitive adhesive and a carrier layer (such as a polyethylene terephthalate layer), a bonding layer (such as a solvent-assisted bonding layer), or a layer resulting from a process performed upon the top and bottom substrates (such as ultrasonic welding) without necessarily introducing additional materials or pieces. Although the adhesive layer has a nominal thickness, it is typically the case that, for example, due to variation in the manufactured thickness of the pressure-sensitive adhesive or in the pressure applied during its application, the actual thickness of the layer is different from the nominal thickness. For example, the two substrates may be bonded using a pressure-sensitive adhesive layer with a nominal thickness that is configured to separate the opposing surfaces by a separation of 100 micrometers. In such a case, variation in the manufactured thickness of the pressure-sensitive adhesive layer or in the pressure applied during its application may result in a final thickness that may lie, for example, as far as 20 micrometers greater or less than the nominal thickness.

Typically, an optical measurement is performed on the sample. For example, the density of a component may be determined by performing a count of the component within a microscopic image. Similarly, the concentration and/or density of a component may be measured by performing optical absorption, transmittance, fluorescence, and/or luminescence measurements upon the sample. Without being bound by theory, an uncertainty of 20 percent in the distance separating the two opposing surfaces (as described in the above example), may, in turn, correspond to 20 percent uncertainty in parameters of the sample that are derived from the optical measurements that are performed upon the sample (such as, the derived concentration and/or density of a component within the sample).

For example, for some applications, the concentration of a component is determined by measuring optical absorption. The absorption measurements are analyzed based upon the Beer-Lambert Law, in accordance with which the resulting optical intensity I after passing through a distance h in a sample containing concentration $\rho$ of a substance with absorptivity coefficient $\alpha$ is $I=I_0 \times e^{-\alpha \rho h}$, where $I_0$ is incident the light intensity before passing through the sample. Thus, for some applications, when passing light through a sample within a sample chamber having a height h (which is defined by the distance between the opposing surfaces), I and $I_0$ are measured and the concentration of a given component is deduced using the known height and the known absorptivity coefficient of the component. For example, such a technique may be used to measure the hemoglobin concentration of a blood sample (e.g., using absorption techniques that are known in the art, such as, by first staining hemoglobin using a suitable dye that provides an optical absorption signature, or by performing the measurements upon unstained hemoglobin). For some applications, additional measurements are performed at different wavelengths to further improve the accuracy in determining the concentration. For such techniques, uncertainty in the height h of the sample chamber results in a corresponding uncertainty in the derived concentration.

For some applications, the density (e.g. count per unit volume) of a component is measured. For example, such measurements may be performed in order to count the number of red blood cells, white blood cells, platelets, reticulocytes, Howell-Jolly bodies, bacteria, and/or parasites of a given type per unit volume, such as when performing a complete blood count or a diagnostic test. Typically, for such applications, images (e.g., microscopic images) of the sample are acquired, and the count per unit volume is determined based upon the count of the component within the images and the corresponding volume within which the count was measured. As the volume is equal to height times area, any uncertainty in the height of the sample chamber results in uncertainty in the volume, and a corresponding uncertainty in the count per unit volume.

For some applications, one or more of the following measurements are performed upon a sample within a sample chamber: bacteria or virus concentration, contaminant concentration (e.g. in drinking water), turbidity measurement (e.g. in water, urine), and enzymatic assays (including enzyme-linked immunosorbent assays). For such measurements, uncertainty in the height of the sample chamber results in uncertainty in the measurement In accordance with some applications of the present invention, the above-described problems associated with uncertainty relating to the height of a sample chamber are at least partially overcome. Referring again to FIG. 2, sample chamber defines first region 42 and a second region 44. The height of first region 42 of the sample chamber is defined by lower surface 46 that is defined by first substrate 48 and by upper surface 50 that is defined by second substrate 52. The height of second region 44 of the sample chamber is defined by lower surface 46 and by second upper surface 54 that is defined by second substrate 52. As shown second upper surface 54 is stepped with respect to first upper surface 50, and both surfaces 50 and 54 are parallel to lower surface 46. The first and second substrates are bonded to each other by adhesive layer 53, e.g., a pressure-sensitive adhesive, such that absolute height h of the first region 42 (which is shallower) is uncertain, e.g., for the reasons described hereinabove. The step between first upper surface 50 and second upper surface 54, provides a predefined height difference Δh between the first, shallower region and the second, deeper region, such that even though height h of the first region is not known to a sufficient degree of accuracy, the height difference Δh is known to a sufficient degree of accuracy to determine a parameter of the sample, using the techniques described herein.

As shown in FIG. 2, second substrate 52 is shaped to define surfaces 50 and 54, such that surfaces 50 and 54 define the manner in which the height of the one or more sample chambers varies between the first and second regions. Typically, relative manufacturing tolerances within a single substrate, and especially between nearby surfaces, are tighter than manufacturing tolerances on positioning between different substrates or even between opposing surfaces lying within the same substrate. Therefore, it is typically the case that by having a single substrate define the manner in which the height of the one or more sample chambers varies between the first and second regions, the height difference between the first and second regions is relatively precise. For example, second substrate 52 may be manufactured with relatively tight tolerances, for example, using injection molding, embossing or machining.

An illustrative example of how the height difference Δh may be used to determine a parameter of the sample is as follows. In order to determine the density of white blood cells within a blood sample, the number of white blood cells within a microscopic image within a given area A within region 42 may be counted, and the number of white blood cells within the same area within region 44 may also be counted. The difference between these two numbers is equal to the number of white blood cells in a volume equal to area A multiplied by height difference Δh. Therefore, the number of white blood cells within this volume is divided by the known volume, to provide the density of white blood cells per unit volume in the solution that is disposed in the carrier. Typically, this value is used to extrapolate an amount or concentration of white blood cells in a stock sample, from which the solution in the sample carrier was produced.

For some applications, additional steps are performed to reduce the error in estimating the white blood cell density. For example, a choice of height differences may be provided, such that a suitable height difference is chosen, and/or such that measurements obtained across multiple height differences are integrated using a statistical method (e.g. averaging, regression, curve-fitting or other techniques known in the art). For some applications, the above-described technique is performed but with different areas being measured in regions 42 and 44, and with the volume being calculated by correcting for the area difference between the areas that were measured in regions 42 and 44.

For some applications, the above-described technique is used to determine the density (e.g., the count per unit volume) of other components within a blood sample, including but limited to red blood cells, platelets, anomalous white blood cells, circulating tumor cells, reticulocytes, Howell Jolly bodies, pathogens (such as, *Plasmodium* or *Babesia*), etc.

It is noted that although height h of first, shallower region 42 is shown in FIG. 2 as being defined solely be the thickness of adhesive layer 53, the height h may be defined by a combination of the adhesion layer and protrusions or extrusions from first substrate 48 and/or second substrate 52. For some applications, the thickness of the adhesive layer varies not only between sample carriers, but even in the same carrier or even along a single sample chamber. Such variation may affect absolute height h of the first region or the height difference between the first and second regions. If this variation is known in advance, it is typically factored into calculations that are performed upon the optical measurements. Typically, the variation in the thickness of the adhesive layer is less than 10 percent along the regions upon which the optical measurements are performed.

It is further noted that, although in FIG. 2 regions 42 and 44 are shown as being regions within a single sample chamber without any separation between the two regions, for some applications, regions 42 and 44 are regions within respective sample chambers that are at least partially separated from each other. In accordance with some applications, the chambers are positioned adjacent to one another, in a linear array, or in any regular lattice shape. For some applications, the chambers are separated from one another by an adhesive layer or a spacer. For some applications, the chambers are positioned adjacent to one another and are filled with the sample using capillary forces. Typically, for such applications, the sample is inserted into the sample carrier via an entry hole, and the sample chamber defines an air exit hole via which air exits the sample carrier, in order to facilitate filling of the sample carrier with the sample. For some such applications, the sample chambers are arranged such that the chamber that has the greatest height is closest to the entry hole, and the sample chamber that has the lowest height is closest to the to the air exit hole, with any additional chambers being arranged in corresponding height order.

For some applications, an optical measurement is performed by providing optical windows on the sample carrier. For example, absorption measurements may be performed by illuminating a sample through a region of one of the substrates (e.g., top substrate 52) that defines an optical window 60 and measuring light coming out through a region of the other substrate (e.g. bottom substrate 48) that defines an optical window 62. For some applications, a reflective surface is used to allow the light to enter and exit through the same optical window (e.g., window 60). This may be used, for example, in the case of an absorption or density measurement, with the analysis having to account, for example, for light having gone through the sample twice. For some applications fluorescence is measured using one or more optical windows. For example, epifluorescence measurements may be performed through a single optical window, since the emitted light may be detected through the same optical window as used for excitation light. For some applications, luminescence is measured using one or more optical windows.

Although FIG. 2 shows only upper substrate 52 defining the stepped surfaces, for some applications, both the upper and lower substrates define surfaces that are stepped with respect to one another (or they both define a surface that is sloped or curved, as described hereinbelow). For some applications, only the lower substrate defines surfaces that are stepped with respect to one another (or defines a surface that is sloped or curved, as described hereinbelow). For some applications, measurements are performed in a lateral direction, with respect to the sample carrier, and a substrate that defines the lateral surfaces of the one or more sample chambers defines surfaces that are stepped with respect to one another (or defines a surface that is sloped or curved, as described hereinbelow).

Figure 3:
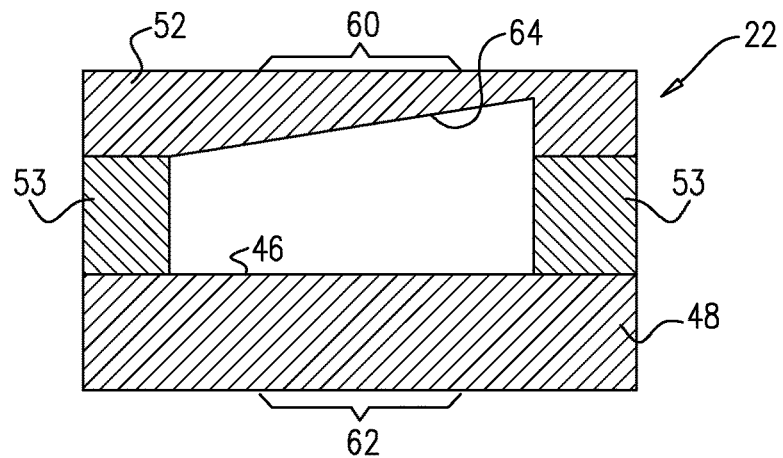
FIG. 3 is a schematic cross-sectional illustration of a sample carrier that defines a variation in height that is gradual, in accordance with some applications of the present invention.

Reference is now made to FIG. 3, which is a schematic illustration of sample carrier 22, in accordance with some applications of the present invention. Sample carrier 22 as shown in FIG. 3 is generally similar to sample carrier 22 as described hereinabove, expect that second substrate 52 is shaped such that the height of the one or more sample chambers varies in a gradual manner. As shown, for some applications, a single sloped surface 64 defined by second substrate 52 defines the manner in which the height of the one or more sample chambers varies. For such applications, the height difference between first and second regions upon which optical measurements are performed is determined based upon the predefined slope of the surface and the relative spacing of the first and second regions upon which the measurements are performed. For some applications, differently shaped surfaces defined by second substrate 52 define the manner in which the height of the one or more sample chambers varies between the first and second regions. For example, a curved surface may be used, which may allow measurements with a larger height difference to be taken in one region versus another region.

Figure 4:
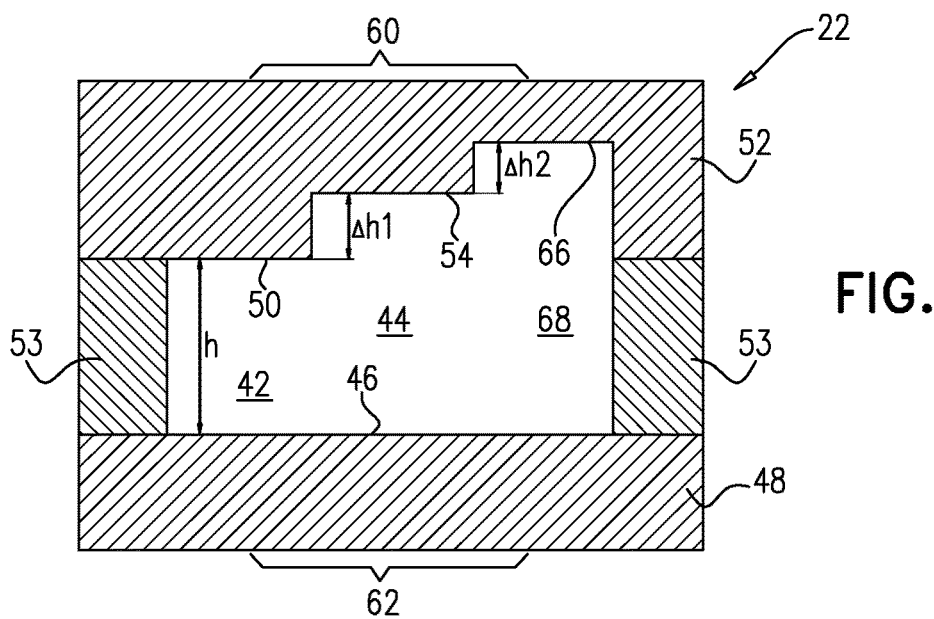
FIG. 4 is a schematic cross-sectional illustration of a sample carrier that includes one or more sample chambers that define first, second, and third regions, the height of the one or more sample chambers varying between each of the first, second, and third regions in a predefined manner, in accordance with some applications of the present invention.

Reference is now made to FIG. 4, which is a schematic cross-sectional illustration of sample carrier 22, the sample carrier including one or more sample chambers that define first region 42, second region 44, and a third region 66, the height of the one or more sample chambers varying between each of the first, second, and third regions in a predefined manner, in accordance with some applications of the present invention. Sample carrier is generally as described hereinabove, except for the differences described below. As shown, the height of the second region is greater than the height of the first region by a height difference $\Delta h1$, and the height of the third region is greater than the height of the second region by a height difference $\Delta h2$ (such that the height of the third region is greater than the height of the first region by a height difference $(\Delta h1+\Delta h2)$). The height differences between the regions are defined by three surfaces 50, 54, and 66 defined by second substrate 52, each of the three surfaces opposing surface 46, defined by first substrate 48. It is noted that the scope of the present invention includes using a sample carrier that defines more than three regions (e.g., 4-10 regions) having predefined height differences between them, and which are defined by a single substrate, mutatis mutandis.

Figure 5:
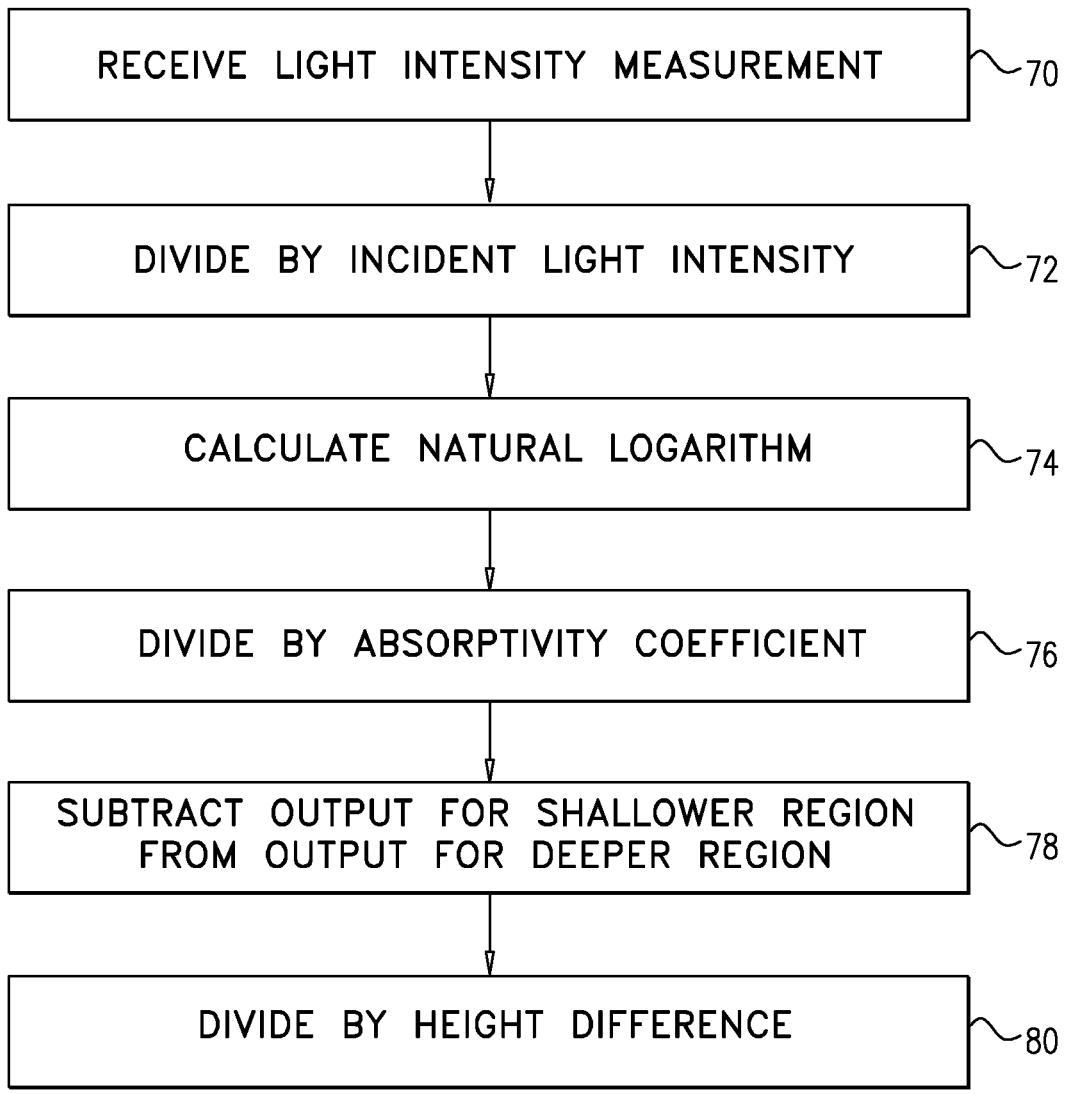
FIG. 5 is a flowchart showing steps of algorithm that is performed in accordance with some applications of the present invention.

Reference is now made to FIG. 5, which is a flowchart showing steps of algorithm that is performed by computer processor 28, in accordance with some applications of the present invention. The flowchart is described with reference to the sample carrier shown in FIG. 2, but the algorithm could be applied to other embodiments of the sample carrier as described herein, mutatis mutandis. For some applications, in order to determine the concentration of a given component within a biological sample that is disposed within sample carrier 22, light is transmitted through regions 42 and 44. The light intensity detected after transmission through these regions is detected by optical measurement device 24, and these light intensity measurements are received by computer processor in step 70. In step 72, for each of these measurements, the detected light intensity is divided by the incident light intensity. In step 74, the natural logarithm of the outputs of step 72 is calculated. In step 76, the outputs of step 74 are divided by the absorptivity coefficient of the component being measured, which provides $\rho \times h$ for region 42 and $\rho \times (h+\Delta_h)$ for region 44. In step 78, the output of step 76 for region 42 is subtracted from the output of step 76 for region 44, which provides $\rho \Delta_h$. In step 80, the output of step 78 is divided by the known height difference, to provide the concentration $\rho$.

For some applications, three or more regions having a known height variation between them are used (e.g., using a sample chamber as shown in FIG. 4), and the algorithm shown in FIG. 5 is repeated with respect to respective pairs of regions with known height differences between them, such that the concentration of the component is determined using different combinations of measured light intensities. Typically, measurements obtained across multiple height differences are integrated using a statistical method (e.g. averaging, regression, curve-fitting or other techniques known in the art), in order to provide a final determination of the concentration of the component. For some applications, discrepancies between the different measurements are used as an indication that there are errors in the measurement or that the sample preparation was not performed correctly (e.g., due to unsuccessful filling of the sample carrier, resulting in remaining bubbles, or untreated blood, etc.). For some applications, in response thereto, a sample is rejected from being used, and/or the computer processor determines that the results obtained for the sample should be treated with a decreased level of confidence relative to other samples or portions thereof, and a corresponding indication is generated upon the output device.

For some applications, the intensity of light that is reflected from the sample is measured, rather than measuring light that is transmitted from the sample. For such applications, the algorithm described with reference to FIG. 5 is modified accordingly.

For some applications, similar techniques are applied to optical measurements that relate to fluorescence or luminescence optical signatures. For example, the detected luminescence of a sample may be proportional to the volume assayed by an optical detector, which in turn may be proportional to sample height. The techniques described herein allow a practitioner to perform the measurement in two or more separate regions of the device that have predefined height differences therebetween. For some applications, the height differences are known to a greater degree of accuracy than the overall height of the sample chamber, as described hereinabove. For some applications, the height differences are used, for example, to mathematically infer sample luminescence per unit volume, which in turn may be used to assess the concentration, count or density of a component of the sample.

For some application, the techniques described with reference to FIG. 5 are used in order to determine the concentration of hemoglobin and/or other components within a blood sample.

As described hereinabove, for some applications concentration is determined by comparing the light intensity before passing through the sample to the measured light intensity after light has been transmitted through, or reflected by, the sample. As the measured light intensity may be up to a few orders of magnitude smaller than the transmitted light intensity, this may require the ability to provide accurate light intensity measurements over a large dynamic range of measured intensities. Alternatively, one may provide the incident light and measure the transmitted or reflected light at a range of different emitter or detector settings, in which case this may require precise knowledge of how the emitter or detector behavior changes with changing the settings (e.g. how emitted light intensity varies with input current).

For some applications of the present invention, the concentration of a given component within the sample is determined without requiring knowledge of the intensity of the transmitted light intensity, by comparing measured light intensities corresponding to respective regions within the sample carrier, and without changing the intensity of the incident light between measurements. For example, with reference to the sample carrier as shown in FIG. 2, if the measured intensity of light transmitted through region 42 is defined as $I_h$ and the measured intensity of light transmitted through region 42 is defined as $I_{h+\Delta_1}$, the concentration of a given component ρ is given by:

$$\rho = \frac{1}{\alpha \Delta_1} \log \frac{I_h}{I_{h+\Delta_1}}.$$

For some such applications, the actual system setting used is chosen such as to provide desirable operating conditions.

For some applications, sample carrier 22 defines three or more regions with predefined height differences between them, for example, as shown in FIG. 4. For some applications, the regions upon which to perform the measurements are selected, based upon the concentration of one or more components within the sample that is being analyzed, such as to provide a dynamic range of concentrations of the sample that can be measured. For example, for lower concentrations of the sample, absorption through a larger optical length may be measured, while for higher concentrations of the sample, absorption through a smaller optical length may be measured. In order to provide a range of optical lengths via which measurements can be performed, the sample carrier may be shaped to define several regions having different height differences between them (e.g., a second region being greater in height than a first region by 30 micrometers, a third region being greater in height than the second region by 60 micrometers, a fourth region being greater in height than the third region by 120 micrometers, etc.). Alternatively, the sample carrier may be shaped to define several repetitions of the same or a similar height difference (e.g., a second region being greater in height than a first region by 30 micrometers, a third region being greater in height than the second region by 30 micrometers, a fourth region being greater in height than the third region by 30 micrometers, etc.). In the latter case, for low concentration of the sample, one would choose which combination of regions to use, such as to provide a suitable height difference, based upon the concentration of one or more components within the sample. For some applications, the regions upon which measurements are performed are chosen to provide repeated measurements at the same height difference, or to provide a plurality of measurements at different height differences. For some applications, measurements obtained across multiple height differences are integrated using a statistical method (e.g. averaging, regression, curve-fitting or other techniques known in the art), in order to provide a final determination of the concentration of a component.

In general, the scope of the present invention includes (a) providing a sample carrier, such as sample carrier 22 as described herein, (b) categorizing a biological sample, (c) placing the sample into the one or more sample chambers of the sample carrier, and (d) based upon the categorization of the biological sample, selecting one of the regions of the sample carrier upon which to perform optical measurements for measuring a given measurand. For example, if a sample, and/or a monolayer formed by the sample, has a relatively low density of red blood cells, then measurements may be performed upon a region of the sample carrier having a relatively great height, such that there is a sufficient density of cells, and/or such that there is a sufficient density of cells within the monolayer formed by the sample, to provide statistically reliable data. Such measurements may include, for example red blood cell density measurements, measurements of other cellular attributes, (such as counts of abnormal red blood cells, red blood cells that include intracellular bodies (e.g., pathogens, Howell-Jolly bodies), etc.), and/or hemoglobin concentration. Conversely, if a sample, and/or a monolayer formed by the sample, has a relatively high density of red blood cells, then such measurements may be performed upon a region of the sample carrier having a relatively low height, for example, such that there is a sufficient sparsity of cells, and/or such that there is a sufficient sparsity of cells within the monolayer of cells formed by the sample, that the cells can be identified within microscopic images. For some applications, such methods are performed even without the variation in height between the regions of the one or more sample chambers being precisely known.

For some applications, the sample is categorized based on receiving an indication of the categorization of the sample (e.g., the sample may be labelled to indicate its categorization and this categorization may be inputted into the computer processor). Alternatively or additionally, the categorization includes performing microscopic imaging upon the sample, and/or measuring a parameter of the sample, such as optical absorption, transmittance, fluorescence, and/or luminescence measurements, by performing a preliminary optical measurement upon the sample. For some applications, the sample is categorized based on the concentration of one or more components within the sample, and/or based on the density (e.g., a count per unit volume) of one or more components within the sample. For some applications, a monolayer is formed within the sample carrier (for example, using techniques as described in U.S. Pat. No. 9,329,129 to Pollak, which is incorporated herein by reference), and the sample is categorized based upon a surface density of one or more components of the sample within the monolayer.

For some applications, based upon the measurand that is being measured, the region within the sample carrier upon which to perform optical measurements is selected. For example, a region of the sample chamber having a relatively great height may be used to perform a white blood cell count (e.g., to reduce statistical errors which may result from a low count in a shallower region), white blood cell differentiation, and/or to detect more rare forms of white blood cells. Conversely, in order to determine mean corpuscular hemoglobin (MCH), mean corpuscular volume (MCV), red blood cell distribution width (RDW), red blood cell morphologic features, and/or red blood cell abnormalities, optical measurements (e.g., microscopic images) may be obtained from a region of the sample chamber having a relatively low height, since in such regions the cells are relatively sparsely distributed across the area of the region, and/or form a monolayer in which the cells are relatively sparsely distributed. Similarly, in order to count platelets, classify platelets, and/or extract any other attributes (such as volume) of platelets, optical measurements (e.g., microscopic images) may be obtained from a region of the sample chamber having a relatively low height, since within such regions there are fewer red blood cells which overlap (fully or partially) with the platelets in microscopic images, and/or in a monolayer.

In accordance with the above-described examples, it is preferable to use a region of the sample carrier having a lower height for performing optical measurements for measuring some measurands within a sample (such as a blood sample), whereas it is preferable to use a region of the sample carrier having a greater height for performing optical measurements for measuring other measurands within such a sample. Therefore, for some applications, a first measurand within a sample is measured, by performing a first optical measurement upon a portion of the sample that is disposed within a first region of the sample carrier, and a second measurand of the same sample is measured, by performing a second optical measurement upon a portion of the sample that is disposed within a second region of the sample carrier. For some applications, the first and second measurands are normalized with respect to each other, for example, using techniques as described in a PCT application being filed on even date herewith, entitled "Performing optical measurements on a sample," which is incorporated herein by reference.

For some applications, a sample carrier as described herein is used to determine hemoglobin concentration within an undiluted blood sample using green light (500 nm-600 nm). For some such applications, the nominal height of the lowest region of the sample carrier is between greater than 1 micrometer, and/or less than 300 micrometers (e.g., 1-300 micrometers). Typically, the predefined height differences between regions of the sample carrier are greater than 5 micrometers and/or less than 500 micrometers (e.g., 5-500 micrometers). For some applications, the area of each of the regions is less than 100 square millimeters, e.g., less than 25 square millimeters, although the exact dimensions typically depend on the substrate that is used and the fabrication method.

For some applications, a sample carrier as described herein is configured such that first and second regions of the sample chambers (which are as described hereinabove) are imaged using a microscope (e.g., by providing optical windows, as described hereinabove). For some such applications, the nominal height of the lowest region of the sample carrier is between greater than 40 micrometers, and/or less than 450 micrometers (e.g., 4-450 micrometers). For some applications, the area of each of the regions that is configured to be imaged by the microscope is less than 400 square millimeters.

Figure 6:
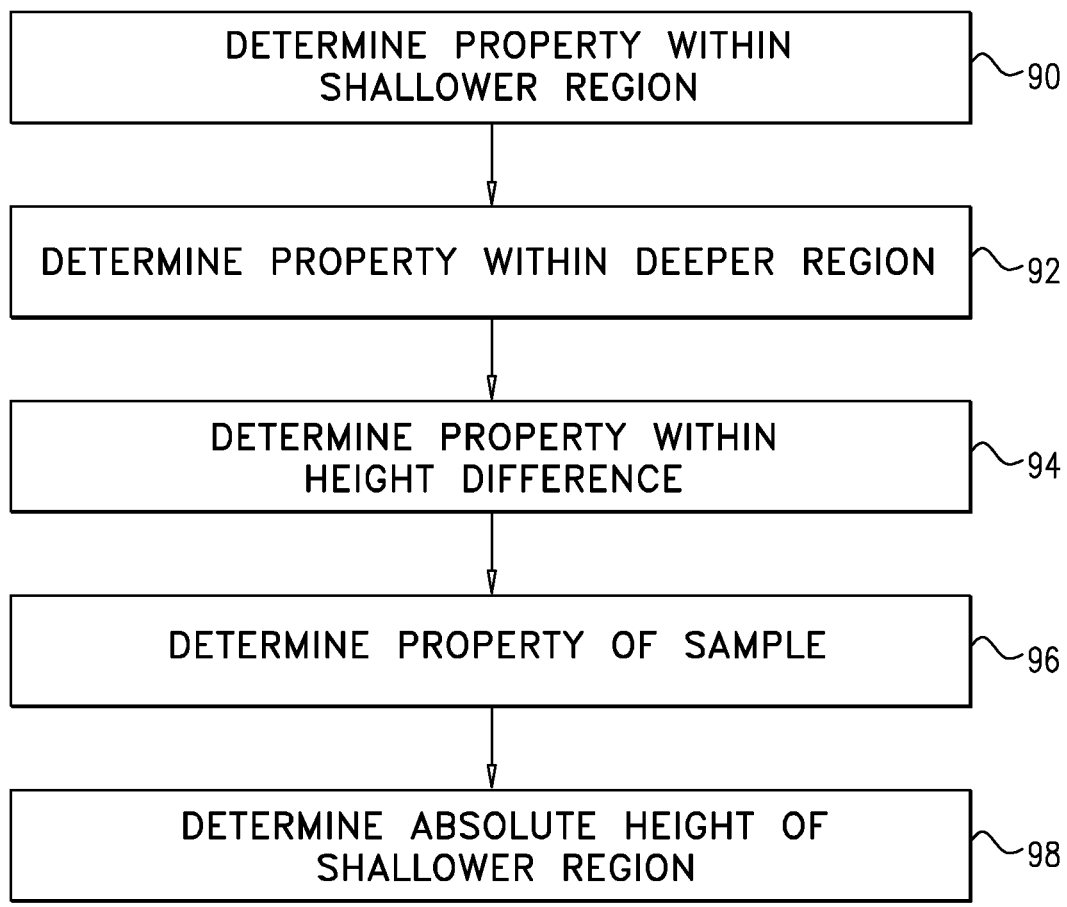
FIG. 6 is a flowchart showing steps of algorithm that is performed in accordance with some applications of the present invention.

Reference is now made to FIG. 6, which is a flowchart showing steps of an algorithm that is performed, in accordance with some applications of the present invention. The flowchart is described with reference to the sample carrier shown in FIG. 2, but the algorithm could be applied to other embodiments of the sample carrier as described herein, mutatis mutandis. For some applications, the algorithm shown in FIG. 6 is used to determine the actual height h of region 42 of sample carrier 22. In a first step 90, an optical measurement is received from the first, shallower region 42, and a property of the sample within the region is determined, the property corresponding to height h. For example, white blood cell count within region 42 may be measured. In a second step 92, an optical measurement is obtained from the second, deeper region 44, and a property of the sample within region 44 is determined, the property corresponding to height h+Δh. For example, white blood cell count within region 44 may be measured. In a third step 94, the property within the height difference Δh is determined. For example, the white blood cell count within the height difference may be determined by subtracting the white blood cell count from shallower region 42 from the white blood cell count from deeper region 44 (assuming that the areas measured in both of the regions were equal). In a fourth step 96, a property of the sample is determined based upon the known height difference and the property within the height difference. For example, the white blood cell count per unit volume may be determined based upon the white blood cell count within the height difference and the known height difference. In a fifth step 98, height h is calculated based upon the determined property of the sample and the property that was obtained in step 90 within region 42. For example, based on the white blood cell count within region 42, and the determined white blood cell count per unit volume within the sample, the volume of region 42 is derived, based upon which height h is derived.

For some applications, the sample as described herein is a sample that includes blood or components thereof (e.g., a diluted or non-diluted whole blood sample, a sample including predominantly red blood cells, or a diluted sample including predominantly red blood cells), and parameters are determined relating to components in the blood such as platelets, white blood cells, anomalous white blood cells, circulating tumor cells, red blood cells, reticulocytes, Howell-Jolly bodies, etc.

In general, it is noted that although some applications of the present invention have been described with respect to a blood sample, the scope of the present invention includes applying the apparatus and methods described herein to a variety of samples. For some applications, the sample is a biological sample, such as, blood, saliva, semen, sweat, sputum, vaginal fluid, stool, breast milk, bronchoalveolar lavage, gastric lavage, tears and/or nasal discharge. The biological sample may be from any living creature, and is typically from warm blooded animals. For some applications, the biological sample is a sample from a mammal, e.g., from a human body. For some applications, the sample is taken from any domestic animal, zoo animals and farm animals, including but not limited to dogs, cats, horses, cows and sheep. Alternatively or additionally, the biological sample is taken from animals that act as disease vectors including deer or rats.

For some applications, similar techniques to those described hereinabove are applied to a non-bodily sample. For some applications, the sample is an environmental sample, such as, a water (e.g. groundwater) sample, surface swab, soil sample, air sample, or any combination thereof. In some embodiments, the sample is a food sample, such as, a meat sample, dairy sample, water sample, wash-liquid sample, beverage sample, and any combination thereof.

Applications of the invention described herein can take the form of a computer program product accessible from a computer-usable or computer-readable medium (e.g., a non-transitory computer-readable medium) providing program code for use by or in connection with a computer or any instruction execution system, such as computer processor 28. For the purposes of this description, a computer-usable or computer readable medium can be any apparatus that can comprise, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Typically, the computer-usable or computer readable medium is a non-transitory computer-usable or computer readable medium.

Examples of a computer-readable medium include a semiconductor or solid state memory, magnetic tape, a removable computer diskette, a random-access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor (e.g., computer processor 28) coupled directly or indirectly to memory elements (e.g., memory 30) through a system bus. The memory elements can include local memory employed during actual execution of the program code, bulk storage, and cache memories which provide temporary storage of at least some program code in order to reduce the number of times code must be retrieved from bulk storage during execution. The system can read the inventive instructions on the program storage devices and follow these instructions to execute the methodology of the embodiments of the invention.

Network adapters may be coupled to the processor to enable the processor to become coupled to other processors or remote printers or storage devices through intervening private or public networks. Modems, cable modem and Ethernet cards are just a few of the currently available types of network adapters.

Computer program code for carrying out operations of the present invention may be written in any combination of one or more programming languages, including an object-oriented programming language such as Java, Smalltalk, C++ or the like and conventional procedural programming languages, such as the C programming language or similar programming languages.

It will be understood that blocks of the flowcharts shown in FIGS. 5 and 6 and combinations of blocks in the flowcharts, can be implemented by computer program instructions. These computer program instructions may be provided to a processor of a general-purpose computer, special purpose computer, or other programmable data processing apparatus to produce a machine, such that the instructions, which execute via the processor of the computer (e.g., computer processor 28) or other programmable data processing apparatus, create means for implementing the functions/acts specified in the flowcharts and/or algorithms described in the present application. These computer program instructions may also be stored in a computer-readable medium (e.g., a non-transitory computer-readable medium) that can direct a computer or other programmable data processing apparatus to function in a particular manner, such that the instructions stored in the computer-readable medium produce an article of manufacture including instruction means which implement the function/act specified in the flowchart blocks and algorithms. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowcharts and/or algorithms described in the present application.

Computer processor 28 is typically a hardware device programmed with computer program instructions to produce a special purpose computer. For example, when programmed to perform the algorithms described with reference to FIGS. 5 and 6, computer processor 28 typically acts as a special purpose sample-analysis computer processor. Typically, the operations described herein that are performed by computer processor 28 transform the physical state of memory 30, which is a real physical article, to have a different magnetic polarity, electrical charge, or the like depending on the technology of the memory that is used.

The apparatus and methods described herein may be used in conjunction with apparatus and methods described in any one of the following patent applications, all of which are incorporated herein by reference:

US 2012/0169863 to Bachelet;
US 2014/0347459 to Greenfield;
US 2015/0037806 to Pollak;
US 20150316477 to Pollak;
US 20160208306 to Pollak;
US 20160246046 to Yorav Raphael;
US 20160279633 to Bachelet;
WO 16/030897 to Yorav Raphael;
WO 17/046799 to Eshel;
WO 17/168411 to Eshel.

There is provided, in accordance with some applications of the present invention, the following inventive concepts:

1. A method for performing optical measurements on a biological sample, the method comprising:

providing a sample carrier that comprises one or more sample chambers configured to house the sample, the one or more sample chambers defining at least first and second regions thereof, a height of the one or more sample chambers varying between the first and second regions;

categorizing the biological sample;

placing the sample into the one or more sample chambers; and based upon the categorization of the biological sample, selecting one of the first and second regions upon which to perform optical measurements for measuring a given measurand.

2. The method according to inventive concept 1, wherein categorizing the sample comprises receiving an indication of the categorization of the sample.

3. The method according to inventive concept 1, wherein categorizing the sample comprises categorizing the sample based upon a density of one or more components within the sample.

4. The method according to inventive concept 1, wherein categorizing the sample comprises categorizing the sample based upon a surface density of one or more components within a monolayer formed by the sample.

5. The method according to inventive concept 1, wherein categorizing the sample comprises categorizing the sample based upon a concentration of one or more components within the sample.

6. The method according to inventive concept 1, wherein categorizing the sample comprises categorizing the sample based upon a count of one or more components within the sample.

7. The method according to inventive concept 1, wherein categorizing the sample comprises measuring a parameter of the sample selected from the group consisting of: optical absorption, transmittance, fluorescence, and luminescence, by performing a preliminary optical measurement upon the sample.

8. The method according to inventive concept 1, wherein categorizing the sample comprises performing microscopic imaging upon the sample.

9. The method according to inventive concept 1, wherein selecting one of the first and second regions upon which to perform optical measurements for measuring the given measurand comprises selecting one of the first and second regions upon which to perform counting of a given component within the sample, by performing microscopic imaging upon the region.

10. The method according to inventive concept 1, wherein selecting one of the first and second regions upon which to perform optical measurements for measuring the given measurand comprises selecting one of the first and second regions upon which to measure a concentration of a given component within the sample, by measuring a parameter selected from the group consisting of: optical absorption, transmittance, fluorescence, and luminescence.

11. The method according to any one of inventive concepts 1-10, wherein:
the one or more sample chambers define at least first, second, and third regions thereof, a height of the one or more sample chambers varying between each of the first, second, and third regions in a predefined manner; and
based upon the identified property of the biological sample, selecting two out of the first, second, and third regions upon which to perform, respective, first and second optical measurements for measuring the given measurand.

12. The method according to inventive concept 11, further comprising:
performing the, respective, first and second optical measurements upon the selected two regions; and
measuring the given measurand by using a relationship between the first optical measurement, the second optical measurement, and the predefined variation in height between the selected two regions.

13. The method according to any one of inventive concepts 1-10, wherein the biological sample includes a blood sample, and wherein selecting one of the first and second regions upon which to perform optical measurements for measuring the given measurand comprises selecting one of the first and second regions upon which to perform optical measurements for measuring a given measurand of the blood sample.

14. The method according to inventive concept 13, wherein selecting one of the first and second regions upon which to perform optical measurements for measuring the given measurand comprises selecting one of the first and second regions upon which to measure a concentration of a given component within the blood sample, by measuring a parameter selected from the group consisting of: optical absorption, optical transmittance, fluorescence, and luminescence.

15. The method according to inventive concept 13, wherein selecting one of the first and second regions upon which to perform optical measurements for measuring the given measurand comprises selecting one of the first and second regions upon which to perform counting of a given component within the blood sample, by performing microscopic imaging upon the region.

16. Apparatus for determining a property of a biological sample, the apparatus comprising:
a sample carrier that comprises one or more sample chambers configured to house the sample, the one or more sample chambers defining at least first and second regions thereof, a height of the one or more sample chambers varying between the first and second regions; and
a computer processor configured to:
categorize the biological sample, and
based upon the categorization of the biological sample, select one of the first and second regions upon which to perform optical measurements for measuring a given measurand of the biological sample.

17. A computer software product, for use with a biological sample that is placed within a sample carrier that comprises one or more sample chambers configured to house the sample, the one or more sample chambers defining at least first and second regions thereof, a height of the one or more sample chambers varying between the first and second regions, the computer software product comprising a non-transitory computer-readable medium in which program instructions are stored, which instructions, when read by a computer cause the computer to perform the steps of:
categorizing the biological sample; and
based upon the categorization of the biological sample, selecting one of the first and second regions upon which to perform optical measurements for measuring a given measurand of the biological sample.

18. Apparatus for performing optical measurements on a biological sample, the apparatus comprising:
a sample carrier that comprises one or more sample chambers configured to house the sample,
the one or more sample chambers defining at least first, second, and third regions thereof, a height of the one or more sample chambers varying between each of the first, second, and third regions in a predefined manner.

19. A method for performing optical measurements on a biological sample, the method comprising:
providing a sample carrier, the sample carrier including one or more sample chambers configured to house the sample, the one or more sample chambers defining at least first and second regions thereof, a height of the one or more sample chambers varying between the first and second regions;
placing the sample into the one or more sample chambers;
measuring a first measurand, by performing a first optical measurement upon a portion of the sample that is disposed within the first region; and
measuring a second measurand, by performing a second optical measurement upon a portion of the sample that is disposed within the second region.

20. The method according to inventive concept 19, wherein the biological sample includes a blood sample, wherein measuring the first measurand comprises measuring a first measurand of the blood sample performing the first optical measurement upon a portion of the blood sample that is disposed within the first region, and wherein measuring the second measurand comprises measuring a second measurand of the blood sample by performing a second optical measurement upon a portion of the sample that is disposed within the second region.

21. The method according to inventive concept 20, wherein measuring the first measurand of the blood sample comprises determining a count of a first component within the blood sample by performing microscopic imaging upon the portion of the sample that is disposed within the first region, and wherein measuring the second measurand of the blood sample comprises determining a count of a second component within the blood sample by performing microscopic imaging upon the portion of the sample that is disposed within the second region.

22. The method according to inventive concept 20, wherein measuring the first measurand of the blood sample comprises measuring a concentration of a first component within the blood sample, by performing, upon the portion of the sample that is disposed within the first region, an optical measurement of a parameter selected from the group consisting of: optical absorption, transmittance, fluorescence, and luminescence.

23. The method according to inventive concept 22, wherein measuring the second measurand of the blood sample comprises measuring a concentration of a second component within the blood sample, by performing, upon the portion of the sample that is disposed within the second region, an optical measurement of a parameter selected from the group consisting of: optical absorption, transmittance, fluorescence, and luminescence.

24. The method according to inventive concept 22, wherein measuring the second measurand of the blood sample comprises determining a count of a second component within the blood sample by performing microscopic imaging upon the portion of the sample that is disposed within the second region.

25. Apparatus for determining a property of a biological sample, the apparatus comprising:
   a sample carrier that comprises one or more sample chambers configured to house the sample, the one or more sample chambers defining at least first and second regions thereof, a height of the one or more sample chambers varying between the first and second regions; and
   a computer processor configured to:
      measure a first measurand, by receiving a first optical measurement performed upon a portion of the sample that is disposed within the first region; and
      measure a second measurand, by receiving a second optical measurement performed upon a portion of the sample that is disposed within the second region.

26. A computer software product, for use with a biological sample that is placed within a sample carrier that comprises one or more sample chambers configured to house the sample, the one or more sample chambers defining at least first and second regions thereof, a height of the one or more sample chambers varying between the first and second regions, the computer software product comprising a non-transitory computer-readable medium in which program instructions are stored, which instructions, when read by a computer cause the computer to perform the steps of:
   measuring a first measurand, by receiving a first optical measurement performed upon a portion of the sample that is disposed within the first region; and
   measuring a second measurand, by receiving a second optical measurement performed upon a portion of the sample that is disposed within the second region.

27. A method for performing optical measurements on a biological sample, the method comprising:
   providing a sample carrier that comprises one or more sample chambers configured to house the sample, the one or more sample chambers defining at least first and second regions thereof, a height of the one or more sample chambers varying between the first and second regions;
   categorizing a measurand of the biological sample that is to be measured;
   placing the sample into the one or more sample chambers; and
   based upon the categorization of the measurand, selecting one of the first and second regions upon which to perform optical measurements for measuring the identified measurand.

28. The method according to inventive concept 27, wherein the biological sample includes a blood sample, wherein categorizing the measurand of the biological sample that is to be measured comprises categorizing a measurand of the blood sample that is to be measured.

29. The method according to inventive concept 28, wherein selecting one of the first and second regions upon which to perform optical measurements for measuring the identified measurand comprises selecting one of the first and second regions upon which to measure a concentration of a given component within the blood sample, by measuring a parameter selected from the group consisting of: optical absorption, transmittance, fluorescence, and luminescence.

30. The method according to inventive concept 28, wherein selecting one of the first and second regions upon which to perform optical measurements for measuring the identified measurand comprises selecting one of the first and second regions upon which to perform microscopic imaging.

31. Apparatus for determining a property of a biological sample, the apparatus comprising:
   a sample carrier that comprises one or more sample chambers configured to house the sample, the one or more sample chambers defining at least first and second regions thereof, a height of the one or more sample chambers varying between the first and second regions; and
   a computer processor configured to:
      categorize a measurand of the biological sample that is to be measured, and
      based upon the categorization of the measurand, select one of the first and second regions upon which to perform optical measurements for measuring the identified measurand.

32. A computer software product, for use with a biological sample that is placed within a sample carrier that comprises one or more sample chambers configured to house the sample, the one or more sample chambers defining at least first and second regions thereof, a height of the one or more sample chambers varying between the first and second regions, the computer software product comprising a non-transitory computer-readable medium in which program instructions are stored, which instructions, when read by a computer cause the computer to perform the steps of:
   categorizing a measurand of the biological sample that is to be measured; and
   based upon the categorization of the measurand, selecting one of the first and second regions upon which to perform optical measurements for measuring the identified measurand.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for determining a property of a biological sample, the method comprising:
   placing the sample into a sample carrier that comprises a plurality of regions, the plurality of regions:
      having upper and lower surfaces,
      having respective heights between the upper and lower surfaces that are different from each other, and
      being configured such that cells within the biological sample form a monolayer of cells on the lower surface within the plurality of regions of the sample carrier,
      the monolayer within respective regions of the sample carrier having respective, different densities from each other, due to the respective regions of the sample carrier having respective heights that are different from each other;
   acquiring microscopic images of each of the plurality of regions; and
   using a computer processor:
      performing measurements upon cell types that have a relatively high density upon microscopic images of the monolayer within a region of the sample chamber having a relatively low height; and performing measurements upon cell types that have a relatively low density upon microscopic images of the monolayer within a region of the sample chamber having a relatively great height.

2. The method according to claim 1, wherein a height of a lowest region of the sample chamber that is configured to house the sample is between 40 and 450 micrometers.

3. The method according to claim 1, wherein an area of the monolayer within each of the regions of the sample carrier that is configured to be imaged by the microscope is less than 400 square millimeters.

4. The method according to claim 1, wherein the biological sample includes a blood sample, and wherein:

performing measurements upon cell types that have the relatively high density upon microscopic images of the monolayer within the region of the sample chamber having the relatively low height comprises performing one or more measurements upon red blood cells upon microscopic images of the monolayer within the region of the sample chamber having the relatively low height, and performing measurements upon cell types that have the relatively low density upon microscopic images of the monolayer within the region of the sample chamber having the relatively great height comprises performing one or more measurements upon white blood cells upon microscopic images of the monolayer within the region of the sample chamber having the relatively great height.

5. The method according to claim 4, wherein performing one or more measurements upon red blood cells upon microscopic images of the monolayer within the region of the sample chamber having the relatively low height, comprises performing one or more measurements selected from the group consisting of: mean corpuscular hemoglobin (MCH), mean corpuscular volume (MCV), red blood cell distribution width (RDW), red blood cell morphologic feature detection, and red blood cell abnormality detection.

6. The method according to claim 4, wherein performing one or more measurements upon white blood cells upon microscopic images of the monolayer within the region of the sample chamber having the relatively great height comprises performing a white blood cell count upon the microscopic images of the monolayer within the region of the sample chamber having the relatively great height.

7. The method according to claim 4, wherein performing one or more measurements upon white blood cells upon microscopic images of the monolayer within the region of the sample chamber having the relatively great height comprises performing white blood cell differentiation upon microscopic images of the monolayer within the region of the sample chamber having the relatively great height.

8. The method according to claim 4, further comprising, using the computer processor, performing one or more measurements upon platelets upon microscopic images of the monolayer within the region of the sample chamber having the relatively low height.

9. The method according to claim 8, wherein performing one or more measurements upon platelets comprises performing one or more measurements selected from the group consisting of: a platelet count, platelet classification, and platelet volume.

* * * * *